United States Patent
Fujita et al.

(10) Patent No.: US 11,937,902 B2
(45) Date of Patent: Mar. 26, 2024

(54) BLOOD PRESSURE ESTIMATION DEVICE, BLOOD PRESSURE ESTIMATION METHOD, COMPUTER PROGRAM, AND STORAGE MEDIUM

(71) Applicants: DELTA TOOLING CO., LTD., Hiroshima (JP); HIROSHIMA UNIVERSITY, Higashihiroshima (JP)

(72) Inventors: Etsunori Fujita, Higashihiroshima (JP); Masao Yoshizumi, Hiroshima (JP); Yumi Ogura, Higashihiroshima (JP); Kanako Takaichi, Aki-gun (JP); Shinichiro Maeda, Aki-gun (JP); Yoshika Nobuhiro, Aki-gun (JP)

(73) Assignees: DELTA TOOLING CO., LTD., Hiroshima (JP); HIROSHIMA UNIVERSITY, Higashihiroshima (JP)

( * ) Notice: Subject to any disclaimer, the term of this patent is extended or adjusted under 35 U.S.C. 154(b) by 893 days.

(21) Appl. No.: 16/961,875

(22) PCT Filed: Jan. 11, 2019

(86) PCT No.: PCT/JP2019/000800
§ 371 (c)(1),
(2) Date: Jul. 13, 2020

(87) PCT Pub. No.: WO2019/139155
PCT Pub. Date: Jul. 18, 2019

(65) Prior Publication Data
US 2020/0383588 A1    Dec. 10, 2020

(30) Foreign Application Priority Data
Jan. 13, 2018    (JP) .................................. 2018-003887

(51) Int. Cl.
*A61B 5/00* (2006.01)
*A61B 5/021* (2006.01)
(Continued)

(52) U.S. Cl.
CPC .......... *A61B 5/02108* (2013.01); *A61B 5/026* (2013.01); *A61B 5/316* (2021.01); *A61B 5/318* (2021.01); *A61B 5/6823* (2013.01)

(58) Field of Classification Search
CPC ..... A61B 5/02108; A61B 5/026; A61B 5/316; A61B 5/318; A61B 5/6823; A61B 5/02116; A61B 5/352
See application file for complete search history.

(56) References Cited

U.S. PATENT DOCUMENTS 5,237,997 A      8/1993  Greubel et al.
10,765,326 B2 *  9/2020  Banet ..................... A61B 5/721
(Continued)

FOREIGN PATENT DOCUMENTS

CN    106037694 A    10/2016
JP    3-505533 A     12/1991
(Continued)

OTHER PUBLICATIONS

International Search Report dated Mar. 19, 2019 in PCT/JP2019/000800 filed on Jan. 11, 2019, citing documents AD, AE and AS—AU therein, 1 page.

*Primary Examiner* — May A Abouelela
(74) *Attorney, Agent, or Firm* — Oblon, McClelland, Maier & Neustadt, L.L.P.

(57) ABSTRACT

Blood pressure is estimated in a non-constraining manner continuously and in real time. A biological signal collected from a person's dorsal part is analyzed, vibration in the human body ascribable to a blood flow rate change in a period from the ventricular filling period to the isovolumet-
(Continued)

ric systole is captured, and the state of fluctuation of an index indicating the state of the in vivo vibration is further captured. This fluctuation index correlates with a person's blood pressure. Therefore, it is possible to estimate whether the blood pressure is in a range indicating a normal-range blood pressure or in a range indicating a high blood pressure, only by having the person sit or lie supine on a surface provided with a biological signal measurement device to measure a biological signal in a non-constraining manner, so as to make the biological signal measurement device contiguous with the person's dorsal part.

9 Claims, 26 Drawing Sheets

(51) Int. Cl.
*A61B 5/026* (2006.01)
*A61B 5/316* (2021.01)
*A61B 5/318* (2021.01)

(56) References Cited

U.S. PATENT DOCUMENTS

| | | | | |
|---|---|---|---|---|
| 10,849,509 | B2* | 12/2020 | Zhang | A61B 5/021 |
| 11,058,314 | B1* | 7/2021 | Galgalikar | A61B 5/02055 |
| 2012/0259181 | A1 | 10/2012 | Fujita et al. | |
| 2013/0030256 | A1 | 1/2013 | Fujita et al. | |
| 2015/0327803 | A1 | 11/2015 | Fujita et al. | |
| 2017/0188848 | A1* | 7/2017 | Banet | G01G 19/50 |
| 2017/0238815 | A1* | 8/2017 | Luxon | A61B 5/021 |
| 2018/0020931 | A1* | 1/2018 | Shusterman | A61N 1/3627 |
| | | | | 600/483 |
| 2018/0070837 | A1* | 3/2018 | Huijbregts | A61B 5/0261 |
| 2018/0098709 | A1* | 4/2018 | Hirsh | A61B 7/04 |
| 2018/0264258 | A1* | 9/2018 | Cheng | A61B 5/25 |
| 2018/0360315 | A1 | 12/2018 | Fujita et al. | |
| 2019/0099088 | A1* | 4/2019 | Whinnett | A61N 1/3925 |
| 2019/0133516 | A1* | 5/2019 | Banet | A61B 5/0537 |
| 2019/0159688 | A1* | 5/2019 | De Groot | A61B 5/02007 |
| 2019/0231274 | A1* | 8/2019 | Ghosh | A61B 5/316 |
| 2020/0100686 | A1* | 4/2020 | Sun | A61B 5/02108 |
| 2021/0000351 | A1* | 1/2021 | Murali | A61B 5/25 |

FOREIGN PATENT DOCUMENTS

| | | |
|---|---|---|
| JP | WO2011/046178 A1 | 4/2011 |
| JP | 2011-167362 A | 9/2011 |
| JP | 2014-117425 A | 6/2014 |
| JP | 2014-223271 A | 12/2014 |
| JP | WO2017/099256 A1 | 6/2017 |

* cited by examiner

FIG. 14 continued

TABLE. BLOOD PRESSURE VALUE AND AVERAGE HEART RATE OF EACH SUBJECT

《NORMAL HIGH-VALUE BLOOD PRESSURE》

| Sub. | SBP (mmHg) | DBP (mmHg) | HR (bpm) |
|---|---|---|---|
| 05 | 133 | 83 | 79 |
| 06 | 135 | 76 | 75 |
| 07 | 133 | 82 | 57 |
| 08 | 130 | 81 | 63 |

《OPTIMAL BLOOD PRESSURE》

| Sub. | SBP (mmHg) | DBP (mmHg) | HR (bpm) |
|---|---|---|---|
| 11 | 108 | 65 | 72 |
| 12 | 119 | 76 | 72 |
| 13 | 118 | 69 | 87 |
| 14 | 105 | 60 | 53 |
| 15 | 108 | 68 | 69 |
| 16 | 113 | 65 | 73 |
| 17 | 106 | 61 | 80 |
| 18 | 117 | 68 | 68 |

《HIGH BLOOD PRESSURE》

| Sub. | SBP (mmHg) | DBP (mmHg) | HR (bpm) |
|---|---|---|---|
| 01 | 164 | 116 | 84 |
| 02 | 148 | 103 | 72 |
| 03 | 141 | 92 | 75 |
| 04 | 142 | 92 | 65 |

《NORMAL BLOOD PRESSURE》

| Sub. | SBP (mmHg) | DBP (mmHg) | HR (bpm) |
|---|---|---|---|
| 09 | 122 | 79 | 84 |
| 10 | 124 | 76 | 74 |

《LOW BLOOD PRESSURE》

| Sub. | SBP (mmHg) | DBP (mmHg) | HR (bpm) |
|---|---|---|---|
| 19 | 96 | 64 | 68 |
| 20 | 97 | 59 | 83 |

FIG. 15 continued

BLOOD PRESSURE ESTIMATION DEVICE, BLOOD PRESSURE ESTIMATION METHOD, COMPUTER PROGRAM, AND STORAGE MEDIUM

TECHNICAL FIELD

The present invention relates to an art for estimating blood pressure by using biological signals obtained from the dorsal part of a person.

BACKGROUND ART

In Patent Documents 1 to 4 and so on, the present inventors have proposed an art that captures, in a non-constraining manner, vibration generated on the dorsal body surface of the upper body of a person and estimates the state of the person by analyzing the vibration. The vibration generated on the dorsal body surface of the upper body of a person is vibration propagated from a human body inner part such as the heart and the aorta and contains information on the atrial and ventricular systoles and diastoles, information on vascular wall elasticity which serves as an auxiliary pump for circulation, and information on reflected waves.

In Patent Document 1, slide calculation is performed in which a predetermined time width is set in a time-series waveform of a dorsal body surface pulse wave (aortic pulse wave (APW)) of around 1 Hz extracted from vibration (biological signal) propagated through the body surface, to find a frequency slope time-series waveform, and from the tendency of its variation, for example, based on whether its amplitude is on the increase or on the decrease, a biological state is estimated. It is also disclosed that, by frequency analysis of the biological signals, power spectra of frequencies respectively corresponding to a function regulation signal, a fatigue reception signal, and an activity regulation signal that belong to a predetermined range from ULF band (ultra-low-frequency band) to VLF band (very-low-frequency band) are found, and the state of a person is determined from time-series variations of the respective power spectra.

Patent Documents 2 to 4 disclose a means for determining a homeostasis function level. For the determination, the means for determining the homeostasis function level uses at least one or more of plus/minus of a differentiated waveform of a frequency slope time-series waveform, plus/minus of an integrated waveform obtained by integrating the frequency slope time-series waveform, absolute values of frequency slope time-series waveforms obtained by absolute value processing of a frequency slope time-series waveform found by a zero-cross method and a frequency slope time-series waveform found by a peak detection method, and so on. By using the combination of these, it is found on which level the homeostasis function is.

PRIOR ART DOCUMENT

Patent Document

Patent Document 1: Japanese Patent Application Laid-open No. 2011-167362
Patent Document 2: WO2011/046178
Patent Document 3: Japanese Patent Application Laid-open No. 2014-117425
Patent Document 4: Japanese Patent Application Laid-open No. 2014-223271

DISCLOSURE OF THE INVENTION

Problems to be Solved by the Invention

According to the aforesaid arts, it is possible to capture a person's state regarding bioregulation functions, namely, a hypnagogic symptom phenomenon, an imminent sleep phenomenon, a low consciousness traveling state, a homeostasis function level, an initial fatigue state, a feeling, and so on.

In a person having a high blood pressure and a person suffering from a heart disease or the like, the blood flow is more affected because of the state of vascular walls, the motion of the heart, and so on than in a healthy person. Conventionally, to determine whether blood pressure is high or not, the blood pressure is usually measured with a blood pressure monitor of a type having a cuff that is to be wound around an arm. However, for the measurement using this, it is necessary to constrain and stabilize the person's body and then attach the device. Therefore, there is a demand for the development of an art that can reduce the person's body constraint and so on as much as possible and more easily measure blood pressure.

The present invention was made in consideration of the above, and has an object to provide an art that uses a biological signal measurement device capable of capturing, in a non-constraining manner, a biological signal propagated through the dorsal body surface of a person, analyzes the obtained biological signal, and estimates blood pressure in a non-constraining manner.

Means for Solving the Problems

To solve the above problem, as a result of studying the correlation between an intake amount of oxygen and blood pressure, the present inventor has focused on the fact that a blood flow rate change accompanying a change in venous return and a change in myocardial contractile force causes a change in blood pressure. Further, left ventricular contraction is a motive force of the systemic circulation of blood, but the right ventricle is present to surround the left ventricle, the left ventricle hides deep in the thoracic cavity on the left part of the median plane, and the pericardium in front of the right ventricle is connected to the anterior chest wall by the sternal pericardial ligament. Therefore, only limited cardiac information is obtained from the anterior chest wall, and in particular, information on the left ventricle which is the motive force of the systemic circulation is difficult to measure from the anterior chest wall. Vibration (in this specification, the term simply mentioned as "vibration" includes sound (acoustic wave)) propagated to the dorsal body surface contains more information on the left ventricle than vibration propagated to the anterior chest wall. Therefore, the present inventor thought that it would be possible to estimate blood pressure by knowing a state of a blood flow rate change from the vibration (biological signal) propagated to the dorsal body surface and has completed the present invention.

Specifically, a blood pressure estimation device of the present invention includes a biological signal processing means which receives a biological signal from a biological signal measurement device set in contact with a dorsal part of a person to capture the biological signal propagated through a body surface of the dorsal part in a non-constraining manner, and which analyzes the received biological signal, wherein the biological signal processing means includes: a filtering means which filters, with a predetermined frequency band, a time-series waveform of the biological signal into a filter-processed waveform in which a cardiac cycle is manifested; a blood flow rate change index calculation means which collates the filter-processed waveform with cardiogram waveform data measured simultaneously with the measurement of the biological signal and obtained from a cardiograph, specifies a waveform component in a range of the time-series waveform from a ventricular filling period to isovolumetric systole in the filter-processed waveform, and finds an index regarding vibration ascribable to a blood flow rate change in a period from the ventricular filling period to the isovolumetric systole; a fluctuation index calculation means which finds a time-series waveform of the index regarding the vibration ascribable to the blood flow rate change and finds an index regarding fluctuation indicating how the found time-series waveform changes; and an estimation means which estimates a blood pressure of the person based on the index regarding the fluctuation by using correlation data for blood pressure estimation which is stored in a storage unit in advance and shows a relation between the index regarding the fluctuation and blood pressure.

The biological signal processing means is capable of continuously estimating the blood pressure of the person by using the biological signals received continuously.

Preferably, the fluctuation index calculation means includes: a fluctuation analysis means which finds the time-series waveform of the index regarding the vibration ascribable to the blood flow rate change, frequency-analyzes the time-series waveform, and generates a fluctuation analysis plot which is a result of the frequency analysis, on a power spectrum-frequency log-log graph; and a fluctuation analysis plot slope calculation means which finds a slope of a regression line of the fluctuation analysis plot, the slope of the regression line of the fluctuation analysis plot being the index regarding the fluctuation.

Preferably, the fluctuation analysis plot slope calculation means is a means which finds, as the slope of the regression line of the fluctuation analysis plot, a slope of the regression line in a predetermined frequency band belonging to a range from VLF to LF, the found slope being the index regarding the fluctuation.

Preferably, the correlation data for blood pressure estimation is formed as correlation data in which the slope of the regression line in the predetermined frequency band belonging to the range from VLF to LF tends to be close to −1 at a normal-range blood pressure and tends to be close to +1 at a high blood pressure.

Preferably, the blood flow rate change index calculation means includes: a scatter plot generation means which specifies one set or more of two waveform components in the range of the time-series waveform corresponding to the ventricular filling period to the isovolumetric systole, in the biological signal, and generates a scatter plot by using total amplitudes of the two waveform components; and a scatter plot slope calculation means which finds a slope of a regression line of a plot group plotted in the scatter plot, the slope of the regression line of the plot group being the index regarding the vibration ascribable to the blood flow rate change.

Preferably, the scatter plot generation means is a means which generates a first scatter plot using total amplitudes of the two waveform components at the time of atrial contraction in the ventricular filling period and a second scatter plot using total amplitudes of the two waveform components corresponding to a timing that is after the two waveform components used in the first scatter plot and near an atrio-ventricular valve closure time which is a shift time to the isovolumetric systole, the estimation means estimates diastolic blood pressure from a fluctuation index that the fluctuation index calculation means finds by using the first scatter plot, and the estimation means estimates systolic blood pressure from a fluctuation index that the fluctuation index calculation means finds by using the second scatter plot.

A blood pressure estimation method of the present invention includes: receiving a biological signal from a biological signal measurement device set in contact with a dorsal part of a person to capture the biological signal propagated through a body surface of the dorsal part in a non-constraining manner; filtering, with a predetermined frequency band, a time-series waveform of the biological signal into a filter-processed waveform in which a cardiac cycle is manifested; collating the filter-processed waveform with cardiogram waveform data measured simultaneously with the measurement of the biological signal and obtained from a cardiograph, specifying a waveform component in a range of the time-series waveform from a ventricular filling period to isovolumetric systole in the filter-processed waveform, and finding an index regarding vibration ascribable to a blood flow rate change in a period from the ventricular filling period to the isovolumetric systole; finding a time-series waveform of the index regarding the vibration ascribable to the blood flow rate change and thereafter finding an index regarding fluctuation indicating how the found time-series waveform changes; and estimating a blood pressure of the person based on the index regarding the fluctuation by using correlation data for blood pressure estimation which is stored in a storage unit in advance and shows a relation between the index regarding the fluctuation and blood pressure.

Preferably, the biological signals are received continuously from the biological signal measurement device, and the blood pressure of the person is continuously estimated.

Preferably, the biological signal is captured while a biological signal detection unit of the biological signal measurement device is disposed in a range from a place corresponding to a position of a clavicle to a place corresponding to a position of a xiphisternum, on the dorsal part of the person.

A computer program of the present invention is a computer program causing a computer to function as a blood pressure estimation device by causing the computer to execute a biological signal processing procedure for receiving a biological signal from a biological signal measurement device set in contact with a dorsal part of a person to capture the biological signal propagated through a body surface of the dorsal part in a non-constraining manner, and analyzing the received biological signal, wherein, as the biological signal processing procedure, the computer is caused to execute: a procedure for filtering, with a predetermined frequency band, a time-series waveform of the biological signal into a filter-processed waveform in which a cardiac cycle is manifested; a procedure for collating the filter-processed waveform with cardiogram waveform data measured simultaneously with the measurement of the biological signal and obtained from a cardiograph, specifying a waveform component in a range of the time-series waveform from a ventricular filling period to isovolumetric systole in the filter-processed waveform, and finding an index regarding vibration ascribable to a blood flow rate change in a period from the ventricular filling period to the isovolumetric systole; a procedure for finding a time-series waveform of the index regarding the vibration ascribable to the blood flow rate change and finding an index regarding fluctuation indicating how the found time-series waveform changes; and a procedure for estimating a blood pressure of the person based on the index regarding the fluctuation by using correlation data for blood pressure estimation which is stored in a storage unit in advance and shows a relation between the index regarding the fluctuation and blood pressure.

Preferably, in the biological signal processing procedure, the computer is caused to execute the estimation of the blood pressure of the person continuously by using the biological signals continuously received.

Preferably, in the procedure for finding the index regarding the fluctuation, the computer is caused to execute: a procedure for finding the time-series waveform of the index regarding the vibration ascribable to the blood flow rate change, frequency-analyzing the time-series waveform, and generating a fluctuation analysis plot which is a result of the frequency analysis, on a power spectrum-frequency log-log graph; and a procedure for finding a slope of a regression line of the fluctuation analysis plot, the slope of the regression line of the fluctuation analysis plot being the index regarding the fluctuation.

Preferably, as the slope of the regression line of the fluctuation analysis plot, a slope of the regression line in a predetermined frequency band belonging to a range from VLF to LF is found, the found slope being the index regarding the fluctuation.

Preferably, in the procedure for finding the index regarding the vibration ascribable to the blood flow rate change, the computer is caused to execute: a procedure for specifying one set or more of two waveform components in the range of the time-series waveform corresponding to the ventricular filling period to the isovolumetric systole, in the biological signal, and generating a scatter plot by using total amplitudes of the two waveform components; and a procedure for finding a slope of a regression line of a plot group plotted in the scatter plot, the slope of the regression line of the plot group being the index regarding the vibration ascribable to the blood flow rate change.

Preferably, as the procedure for generating the scatter plot, a procedure is executed for generating a first scatter plot using total amplitudes of the two waveform components at the time of atrial contraction in the ventricular filling period and a second scatter plot using total amplitudes of the two waveform components corresponding to a timing that is after the two waveform components used in the first scatter plot and near an atrioventricular valve closure time which is a shift time to the isovolumetric systole, and in the procedure for finding the index regarding the fluctuation, diastolic blood pressure is estimated from a fluctuation index found using the first scatter plot, and systolic blood pressure is estimated from a fluctuation index found using the second scatter plot.

A computer-readable storage medium of the present invention stores the aforesaid computer program causing a computer to function as a blood pressure estimation device by causing the computer to execute a biological signal processing procedure for receiving a biological signal from a biological signal measurement device set in contact with a dorsal part of a person to capture the biological signal propagated through a body surface of the dorsal part in a non-constraining manner, and analyzing the biological signal.

Here, the principle based on which blood pressure can be estimated by the present invention will be described. Cardiac output of a person is determined depending on a metabolic demand of the body, and cardiac output is equal to a product of heart rate and stroke volume. Heart rate is controlled by autonomic innervation mainly of a cardiovascular center and humoral control. Cardiac output is influenced by ventricular preload, and stroke volume is determined by cardiac contractile force and preload/afterload. The state of a blood flow rate change can be explained by a mathematical model using the Bernoulli's theorem. The Bernoulli's theorem includes pressure energy, kinetic energy, and elevation energy, which are called pressure head, velocity head, and elevation head in terms of the height of a water column, and the sum of the heads is total head. Energy lost by friction and bending and at output/input ports is head loss proportional to the velocity head, and a governing equation of a flow rate change is found by a function of a blood head of preload/afterload and a flow rate.

By applying these, as a method to know how the blood flow rate of the left ventricle which is the motive force of systemic circulation changes and how the blood flow is controlled, the present inventor considered knowing them from a change in the head loss. Information on a change in vibration (sound) propagated to the dorsal body surface from the heart is formed by a blood flow rate change caused by a change in the contractile force of cardiac muscles. The blood flow rate change is produced by the diastolic performance and systolic performance of the cardiac muscles. A product of cardiac output and the total resistance of peripheral blood vessels is blood pressure, and changes in heart rate and cardiac contractile force cause a change in blood pressure. Blood flows because of a blood pressure gradient. Pulsation is caused by contraction and relaxation, and the pulsation of the heart in which the diastole and the systole occur alternately changes arterial pressure. From this, it follows that a parameter for capturing this change in the arterial pressure is hidden in information on a change in vibration (sound) of the left ventricle. An important point is in which phase of the cardiac cycle the change should be captured. The ventricular cycle can be divided into four periods: a ventricular filling period, isovolumetric systole, an output period, and isovolumetric diastole. The ventricular filling period includes an initial rapid filling period, a slow filling period, and a final filling period due to atrial contraction. The atrial contraction starts with a P wave of a cardiogram. For the natural ventricular filling based on a pressure difference, the left atrium functions as a booster and also becomes the preload of the left ventricle. This preload based on the venous return elevates an end diastolic pressure of the left ventricle. It is known that a blood flow rate change after the atrial contraction correlates with a change in the left cardiac diastolic pressure and a change in heart rate. Here, a clue to knowing the diastolic blood pressure is thought to be in the ventricular filling period, in particular, the filling period due to the atrial contraction.

The steadiness of a blood flow rate change lies in its nature that statistics of an average value, a correlation function (PSD), and so on are constant irrespective of the measurement time. The average value is heart rate, and autonomic nervous system activity is quantified by PSD of a time-series waveform composed of heart rate changes, and it is called heartbeat fluctuation. The heartbeat fluctuation is represented by a numerical value called $1/f^\beta$ fluctuation. If time-series data of heart rate is steady, the logarithmic representation of PSD is in inverse proportion to the logarithmic representation of frequency. If a spectral index $\beta=1$, the fluctuation is called 1/f fluctuation, and a case where $\beta$ is larger than 1 is physiologically defined as non-steady. In other words, in a resting state usually called a steady state, heartbeat fluctuation is the 1/f fluctuation as a whole and presents a fractal Brownian motion. An occasional blood pressure elevation and an antihypertensive keep the fluctuation high. When a periodic component keeping it high is mixed in any time width, heart rate and cardiac contractile force change, which then changes blood pressure. Stress changes blood pressure to cause a blood flow rate change. The blood flow rate change causes a great change and stagnation in PSD of each periodic component to generate a time-dependent time-series signal. The great change and stagnation result in the non-steadiness of the fluctuation of the blood flow rate change.

In the absence of disturbance to a human body, that is, in a stress-free state, the fluctuation of heart rate and blood flow rate is of the $1/f^\beta$ type, and in a person having a normal blood pressure, $\beta=1$ and $1/f^\beta$ is $-1$. In a hypertensive, autonomic innervation and humoral control appear even when he/she is at rest, and a periodic component due to sympathetic innervation is included in the fractal Brownian motion. That is, in a hypertensive, $1/f^\beta$ indicating the fluctuation of heart rate and blood flow rate is approximately $-1$ as a whole, but in this fluctuation, fluctuation in a region including the LF band indicating the state of sympathetic innervation remains high, and in this region, a+component appears.

Further, artificial blood pressure drop by antihypertensive medication causes reflective sympathicotonia to increase cardiac contractility, restraining a change in blood pressure. Further, in a case where reflex regulation of the human body does not work, blood pressure that is decided according to the optimum coupling of a dynamic mutual relation of the ventricle and the arterial system is maintained. hi a situation where the autonomic nervous system works, the human body gives priority to maintaining a preset blood pressure to regulate blood circulation. That is, the integrity of the cardiovascular system is greatly modified by the autonomic nervous system, but it changes depending on a difference in sympathetic responsiveness of the heart and blood vessels, and the integrity state is not maintained. The artificial antihypertensive medication strongly affects the integrity of the cardiovascular system, and in the control by the antihypertensive, it is thought that the fluctuation of a blood flow rate change develops such that a linear portion, that is, the+component appears in part of $1/f^\beta$.

Further, in the governing equation of left cardiac diastolic pressure, an integrated intensity of the fluctuation in a band from VLF to LF, which is a parameter correlating with the autonomic innervation and the humoral control of heart rate, is involved. As for the blood flow rate change and a normalization factor, a cardiac function can be determined from a physical phenomenon caused by blood that has returned to the heart, and the phase is a boundary between the atrial systole and the ventricular systole, with the preload of the ventricle serving as a key. Therefore, an analysis target phase is immediately before/after the isovolumetric systole.

The sympathetic nerves cause an increase in heart rate, an increase in cardiac contractile force, and so on through acceleratory G protein by stimulating a β receptor. It is said that a phenomenon clinically observed in accordance with these sympathicotonia reaches a peak in about fifteen seconds. On the other hand, it is also known that the revelation of the effect of sympathetic nerve stimulation cannot be dynamically adjusted beat by beat of the heart rate. Here, there is thought to be a possibility that, by observing the fluctuation of a heartbeat change and cardiac contractile force in a resting state, it is possible to capture a blood pressure change due to the increase in heart rate and the increase in the cardiac contractile force which are caused by the stimulation of the β receptor. The blood pressure change correlates with the fluctuation of a blood flow rate change, and the blood flow rate change appears in a frequency band of dorsal body surface sound.

Incidentally, the pericardial cavity between the outer pericardium and the inner pericardium contains several ml liquid. The liquid in the pericardial cavity influences the pumping operation of the heart. It is said that, in an adult, the heart weighs 200 to 300 g and a heart sound frequency is 25 to 45 Hz, or to 50 Hz. If the heart sound frequency is assumed to be equal to the natural frequency of a structure in which the heart floats and a dynamic spring constant of the heart floating structure is calculated, it is about 2.5 kg/mm. If this calculation result is regarded as correct, the heart floating structure is considered as having a vibration damping function for high frequencies of 70 Hz or more, while being a rigid body for a low frequency band, and a vibration/acoustic waveform in a low-frequency band of around 25 Hz equal to or lower than the natural frequency is linear/weakly nonlinear information. Therefore, vibration waveforms of 25 Hz or less except a resonance band are to be measured.

Autonomic innervation which is a governing factor of systemic circulation and humoral control by a hormone are distinguished by the integrated intensity of fluctuation in a frequency band of a heartbeat change, and it is said that the integrated intensity of fluctuation in the HF band of 0.15 to 0.4 Hz and that in the LF band of 0.04 to 0.15 Hz represent active states of the parasympathetic nerves and the sympathetic nerves, and the integrated intensity in the VLF band of 0.003 to 0.04 Hz appears owing to humoral control. Then, an empirically obtained increase in VLF contributes to an increase in heart rate on condition that an adrenocorticotropic hormone (ACTH) whose activity is increased by a corticotropin-releasing hormone (CRH) of the paraventricular nucleus of the hypothalamus, the parasympathetic nerves, and epinephrine are increased and the sympathetic nerves and angiotensin are suppressed. Further, what activates both the CRH-ACTH systems and the sympathetic nerves is a stress resistance reaction. Incidentally, it is also known that, at night, since the secretion of melatonin strongly suppresses the sympathetic nervous system, heart rate and blood pressure are kept low despite the increase of the CRH-ACTH system and the activation of the parasympathetic nerves.

The blood flow rate change is expressed by changes in stroke volume and heart rate, and under a measurement state regulated to the resting state and a short time, a stroke volume change is stable, and a heart rate change has a high contribution ratio as a governing factor of the blood flow rate change. VLF and LF are governing factors of the heart rate change and therefore, if the time width for the measurement is found from VLF, it is 360 seconds, and 1/360 thereof is 0.003 Hz, which is a frequency in the VLF band. The diastolic performance and the systolic performance of the left ventricle are considered as having dependence on a blood pressure change, and governing factors of the blood flow rate change are a mass change and a velocity change, the mass change appears as a blood volume change, and the velocity change appears as a heart rate change. For the blood pressure change which becomes an impulse, the mass change and the velocity change are governing factors, and what is generated as a result of the combination of the two factors is an amplitude change (fluctuation) of a time-series waveform. Here, a mathematical model in which a valve is considered as a pipe will be studied.

FIGS. 24(*a*), (*b*) illustrate volume changes of the atria and the ventricles and the movement of blood in a period from the ventricular filling period to the release of a valve in the isovolumetric systole. x represents a line coordinate of the blood moving in the atria/mitral valve/ventricles. Let an inlet of the mitral valve be 0 and let its outlet be x=1. Let a subscript for the inlet be 1 and let a subscript for the outlet be 2. A represents the sectional area of the mitral valve, γ represents the weight of the blood per unit volume, g represents gravitational acceleration, v represents flow velocity, h represents a head of the blood, and P represents pressure.

When the inlet of the mitral valve is x=0, the pressure of the blood is P1=γh1, and a work ΔW1 required to push the blood with the flow rate Q during a time Δt is expressed as follows.

$$\Delta W1 = P1 Q \Delta t = \gamma h1 Q \Delta t \quad (1)$$

Similarly, a work done at an outlet end of the mitral valve is expressed as follows.

$$\Delta W2 = \gamma h2 Q \Delta t \quad (2)$$

Let a pressure loss of a fluid, which is a function of the flow rate Q, be f(Q). Energy ΔT consumed during the time Δt in the mitral valve because of this loss is expressed as follows.

$$\Delta L = \gamma f(Q) Q \Delta t \quad (3)$$

Kinetic energy corresponding to a movement distance dx in the mitral valve is expressed as follows.

$$dK = (V^2/2g) \times A \gamma dx \quad (4)$$

A is the area of the blood and Aγ is the weight of the blood.

Therefore, $$dk = (1/2gA) \times \gamma Q^2 dx \quad (5)$$

Therefore, the kinetic energy K that the blood has is expressed as $$K = \gamma Q^2 m/2 \quad (6),$$

where m is a constant determined by the nature of the mitral valve and is called a valve constant.

A change ΔK in the kinetic energy of the blood in the mitral valve in the short time Δt is found as follows.

$$K = m \gamma Q (dQ/\Delta t) \quad (7)$$

From the relation of $$\Delta K = \Delta W1 - \Delta W2 - \Delta L \quad (8),$$

$$m(dQ/dt) = h1 - h2 - f(Q) \quad (9)$$

is found.

In FIG. 24(a), h1 represents preload and is the pressure head due to atrial contraction, and h2 is afterload and is the pressure head due to ventricular diastolic pressure.

A change in the ventricular diastolic pressure can be found if a time-dependent change in the flow rate Q is given.

Equation (9) can be re-arranged into $$h1 - h2 = m(dQ/dt) + f(Q) \quad (10), \text{ and}$$

central venous pressure and atrial pressure are considered as substantially constant immediately before the atrial contraction, and if the head loss is f(Q)≈0 since IV is small, then $$h1 - h2 = m(dQ/dt) \quad (11).$$

Assuming that the flow rate rapidly and evenly changes from Q0 to 0, an elevation Δ(h1-h2) of the ventricular diastolic pressure is expressed as follows, where Tm is the time required for the mitral valve to close.

$$\Delta(h1-h2) = mQ0/Tm = 1m/gA \times Q0/Tm = 1v0/gTm \quad (12)$$

Here, as for the elevation of the head, it is seen that, as the flow velocity in the rapid filling period is higher and the time required for the mitral valve to close is shorter, water hammering is larger, resulting in big first sound. m is a constant determined by a function of the mitral valve/aortic valve as a pipe. h1 represents the preload and is the atrial pressure determined by the venous return pressure of the atrial contraction and the atrial systolic performance. The afterload is the ventricular internal pressure. Here, h1-h2 correlates with the atrial systolic performance required to push out the blood returning to the ventricle and also correlates with brachial diastolic blood pressure. Further, a difference between left atrial inner pressure and left ventricular internal pressure is h1-h2, and the time when this difference becomes equal is the appearance point of the R wave and is the closure time of the mitral valve.

$$f(Q) = m(dQ/dt) \quad (13)$$

$$\Delta f(Q) \propto dPmax/dt \quad (14),$$

which indicates the possibility that the systolic blood pressure can similarly correlate with a blood volume change near the R wave.

Here, a difference between a hypertensive and a normal subject will be studied. When the ventricle completely expands, blood further flows into the ventricle owing to venous pressure. In the final phase of the filling period, more blood is pushed into the left ventricle owing to left atrial contraction. It is known that, in an adult of his/her twenties to thirties at rest, the volume of blood that flows in owing to atrial contraction is only 10 to 20% of the total volume, but this percentage increases with age up to around 46%. In the hypertensive, a ratio of the blood filling due to left atrial contraction is considered to be higher. A reason for this is that, in the hypertensive, heart rate tends to be relatively higher than when he/she was a young adult of his/her twenties to thirties. The increase in heart rate shortens the time for passive blood filling. A flow rate at this final phase of the filling period is an important factor when the left ventricular filling due to left atrial contraction determines diastolic blood pressure, and this factor is changed by sympathetic nerve stimulation. How this changes is influenced by the secretion of noradrenaline and adrenaline which are neurotransmitters, noradrenaline is coupled with a β1 receptor of a myocardial cell membrane, and adrenaline also acts on the myocardial β1 receptor. Adrenaline and noradrenaline, which are called catecholamine, activate the β1 receptor to increase heart rate and increase contractile force.

Next, in order to convert dQ/dt in Equation (10) to an algebraic equation, the use of the Lorenz plot method as a graphical solution for capturing a blood flow rate change will be described. Using a cardiogram, only a given phase of the ventricular cycle is focused on, and regarding an amplitude change of a time-series waveform corresponding to the given phase, a plot group of adjacent amplitude changes a1, a2 is plotted by the Lorenz plot method. From a set of the amplitudes a1, a2, a slope tanθ (hereinafter, this slope tanθ will be sometimes called "Fractal Angle (FA)") is found by the least squares method. A time-dependent change of the slope tan° is expressed by a time-series waveform, the result of frequency analysis of the time-series waveform is log-log represented, and a slope regarding the frequency and PSD is found. Specifically, a measurement time width is set to 360 seconds as previously described, the slope in 30 seconds is found, and fluctuation of tanθ is plotted with a 90% overlap of 30 seconds, that is, every 3 seconds, and the time-series waveform of a change in tanθ is found. The time-series waveform of the change in tanθ is frequency-analyzed, and a slope in an LF band (this slope will be called "Fractal Slope (FS)") is found from the log-log-representation. Depending on whether the slope FS in the LF band takes a "+" value or a "−" value, it is possible to determine the presence/absence of the activation of the β1 receptor. The "+" value indicates a state in which a periodic component is strong and strong control is performed, and the "−" value indicates the fractal Brownian motion, that is, 1/f fluctuation and a state in which the normal subject is at rest and thus in the steady state and a homeostasis function is exhibited.

From the above, the whole slope of the change in the left cardiac blood flow rate appears in the VLF to LF bands, and a slope that looks different from the whole slope appearing when the sympathetic activity increases also appears in these bands. Further, the slope appearing when the sympathetic activity increases comes in "+" and "−", and especially in the case where the slope presents the "+" value, the neurotransmitters act on the myocardial β1 receptor, and the heart rate imparts periodicity to a frequency component and the blood pressure imparts periodicity to FS, so that the fluctuation is linearized. Heart rate (FIR) control having a double control structure of autonomic innervation and humoral control is found from a PSD-Hz log-log representation showing the frequency analysis result of a time-series waveform of RRI in a cardiogram. The fluctuation found by the frequency analysis of RRI in the cardiogram does not include a fluctuation component occurring from a blood flow rate change due to an increase in the myocardial contractile force caused by the activation of the β1 receptor. The blood flow rate change due to the change in the myocardial contractile force is also influenced by a change in ventricular diastolic pressure which is the afterload. Therefore, the change in ventricular diastolic pressure correlates with the blood flow rate change.

Atrial contractile force generates a pressure exceeding the blood pressure change due to the venous return, and when it exceeds the ventricular diastolic pressure and further exceeds the aortic diastolic pressure which is in an equilibrium state with the ventricular diastolic pressure, the mitral valve closes. An algebraic equation regarding fluctuation of the blood flow rate change immediately before the mitral valve closes and an average brachial diastolic blood pressure and an average brachial systolic blood pressure is expressed as follows using FS (±LF) as a parameter.

$$\Delta(h1-h2)=1/gA \cdot Q_{(\pm LF)}/Tm=1/gA \cdot F_{fs}(\pm LF) \qquad (15)$$

Therefore, the diastolic blood pressure (D.B.P) is as follows.

$$H(D.B.P)=\Delta(h1-h2)+H0=1/gA \cdot Q \cdot F_{fs}(\pm LF)+H0 \qquad (16)$$

Here, since H0 is when FS is 0, it is a value at a boundary between a high blood pressure and a normal-range blood pressure in a resting state. This is because the 1/f fluctuation is −1 in the normal subject at rest. On the other hand, in the hypertensive, since the value of the diastolic blood pressure is high, an LF value having a positive slope correlating with a high heart rate and a high cardiac contractile force is used.

Applying the above-described idea to the ventricular systole makes it possible to estimate systolic blood pressure. The ventricular systole of about 0.35 seconds is composed of the isovolumetric systole and the ventricular output period longer than the isovolumetric systole. As illustrated in FIG. 24(*b*), when the left ventricular pressure rises to exceed the aortic pressure in the isovolumetric systole, the aortic valve opens, so that the ejection of blood from the left ventricle into the aorta starts. The blood output from the left ventricle has a larger energy amount than blood flowing out to peripheral blood vessels and thus expands elastic blood vessels and temporarily stays there, so that the arterial pressure increases to reach the systolic blood pressure. Then, even though the arterial pressure is higher than the left ventricular pressure, the blood continues flowing from the left ventricle to the aorta owing to inertia force. A decrease in blood vessel elasticity is reduced by an energy loss due to blood vessel expansion, and the systolic blood pressure is further increased by reflective waves from the peripheral blood vessels. Then, since the duration of the rapid output period is also shortened, the systolic blood pressure rises. This indicates a possibility that second sound of the hypertensive is larger in amplitude than first sound owing to the combination with the water hammering due to the effect of reducing the closure time of the artery. Here, Equation (9) is converted to an equation corresponding to the phase of the ventricular systole.

The preload is h3 instead of h1 and the phase is the ventricular systole instead of the atrial systole. The afterload is h4 instead of h2. Δh4 represents the ventricular systolic performance and is a parameter related to systolic blood pressure. The phase is a time zone from the vicinity of the end of the R wave in the cardiogram to the isovolumetric systole. dQ/dt correlates with $dP/dt_{max}$ often used as an index of cardiac contractility in the isovolumetric systole, and a change in initially ejected blood flow rate correlates with a change in the left ventricular systolic pressure. The arterial systolic blood pressure highly correlates with a heart rate change and the ventricular systolic performance in the isovolumetric systole, and the equation using LF as the parameter also holds here.

Therefore, the systolic blood pressure (S.B.P.) is represented by an equation including a function Ffs using Ffs as a factor as follows.

$$H(S.B.P)=\Delta h4+H0=1/gA \cdot Q \cdot F_{fs}(\pm LF))+H0 \qquad (17)$$

Effect of the Invention

The present invention is configured to analyze a biological signal collected from the dorsal part of a person, capture vibration in the human body (in vivo vibration) ascribable to a blood flow rate change in a period from the ventricular filling period to the isovolumetric systole, and further captures the state of fluctuation of an index indicating a state of the in vivo vibration fluctuates (index regarding fluctuation (fluctuation index)). The fluctuation index correlates with a person's state, in particular, information on blood pressure as described above. Therefore, according to the present invention, it is possible to easily estimate blood pressure, in particular, estimate whether the blood pressure is in a range indicating a normal-range blood pressure (diastolic blood pressure of less than 90 mmHg, and the systolic blood pressure of less than 140 mmHg) or in a range indicating a high blood pressure, only by having a person sit or lie supine on a vehicle seat, a chair for home, office, or other uses, sleeping equipment such as a bed, or the like provided with a biological signal measurement device that can measure a biological signal in a non-constraining manner and making the biological signal measurement device contiguous with the person's dorsal part. Further, in blood pressure measurement using a cuff, after the measurement is performed once, the upper part of the arm has to be pressed again by the next measurement, and this period needs to be about several minutes, which makes the continuous blood pressure measurement difficult, but according to the present invention, because of no constraint, it is possible to estimate blood pressure continuously ("continuously" mentioned here includes intermittent measurement at a shorter interval than that when the cuff is used), by using biological signals which are captured one after another from the dorsal part.

DESCRIPTION OF EMBODIMENTS

Figure 1:
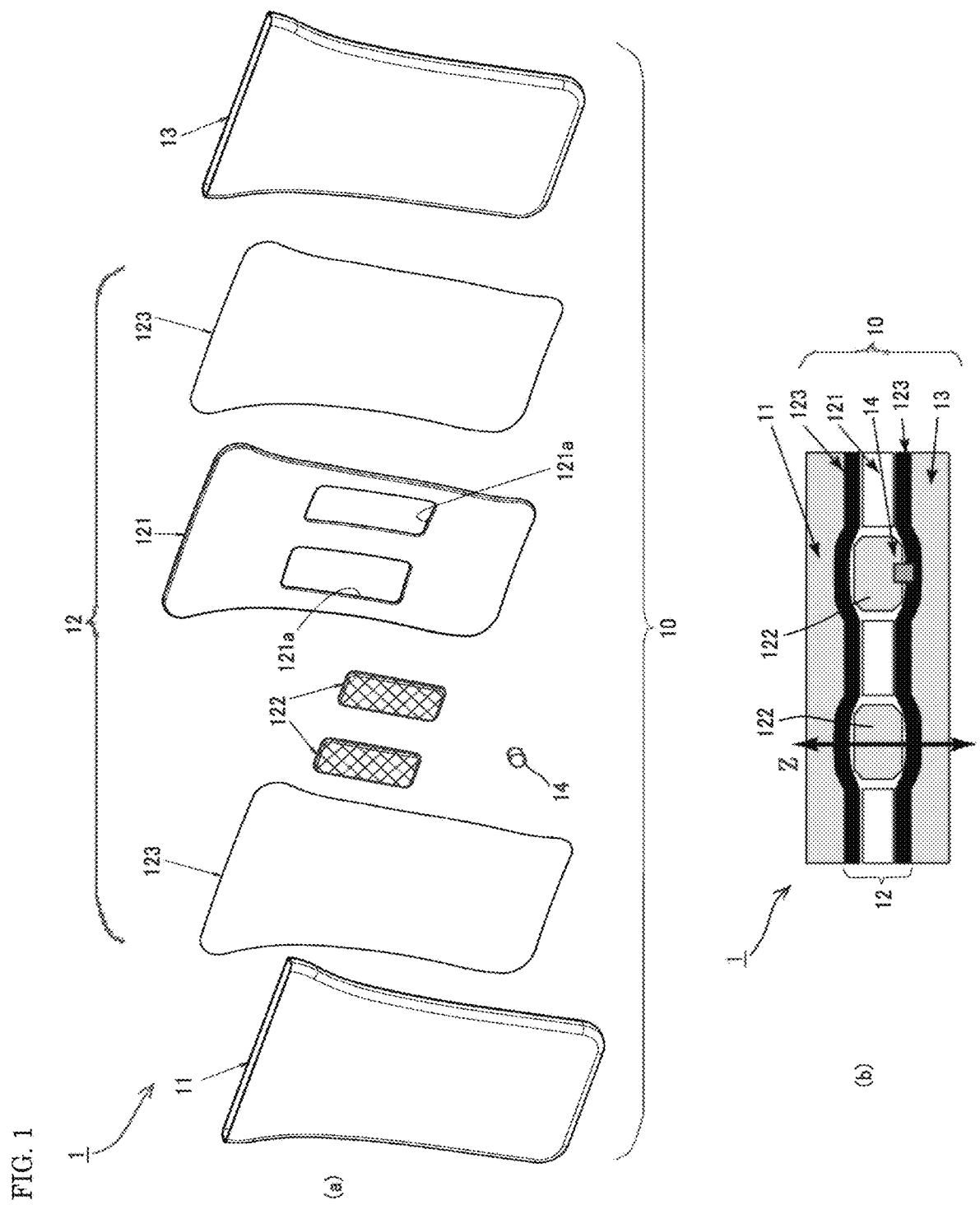
FIG. 1(a) is an exploded view illustrating an example of a biological signal measurement device which measures a dorsal body surface pulse wave and used in one embodiment of the present invention.
FIG. 1(b) is a sectional view of an essential part thereof.

The present invention will be hereinafter described in more detail based on an embodiment of the present invention illustrated in the drawings. In the present invention, a biological signal propagated through the dorsal body surface of a person (dorsal body surface pulse wave) is used. As described above, this dorsal body surface pulse wave is vibration generated when blood flowing in the atria and the ventricles collides with valves and myocardial inner walls in atrial and ventricular systoles and diastoles or vibration caused by the blood pressing the vascular wall when it flows in the aorta (including vibration transmitted as sound), that is transmitted to the body surface. Therefore, the dorsal body surface pulse wave contains information on vibration in a human body in the ventricular filling period, that is, vibration in a human body (in vivo vibration) ascribable to a blood flow rate change in a period from the ventricular filling period to the isovolumetric systole, which is a target of the present invention.

A biological signal measurement device for collecting the dorsal body surface pulse wave preferably uses a biological signal measurement device 1 used in the drowsy driving warning device (Sleep Buster (registered trademark)) manufactured by DELTATOOLING Co., Ltd. FIGS. 1 illustrate the schematic structure of the biological signal measurement device 1. The biological signal measurement device 1 includes a biological signal detection unit 10 besides not-illustrated electrical wiring and so on, and the biological signal detection unit 10 can be used while incorporated in a chair, a bed, a vehicle driver seat, or the like for measurement and is capable of collecting a biological signal without constraining the arm, hand, finger, or the like.

As illustrated in FIGS. 1(a), (b), the biological signal detection unit 10 has a three-layer structure composed of a stack of a first layer member 11, a second layer member 12, and a third layer member 13 which each have a substantially rectangular shape having predetermined width and length. The first layer member 11 is formed of a three-dimensional knitted fabric or the like, and it is used while being placed on a side toward the human body whose biological signal is to be detected, and the biological signal is first propagated to the first layer member 11 through the dorsal body surface of the human body. The second layer member 12 functions as a resonance layer which emphasizes a weak dorsal body surface pulse wave propagated from the first layer member 11, by a resonance phenomenon or a beat phenomenon, and includes a base member 121 formed of a bead foam or the like, three-dimensional knitted fabrics 122 functioning as natural oscillators, and films 123 generating membrane vibration. In the base member 121, two placement holes 121a, 121a are formed at symmetrical positions sandwiching its center, and the three-dimensional knitted fabrics 122, 122 functioning as the natural oscillators are placed in the placement holes 121a, 121a. The films 123, 123 are stacked on surfaces of the second layer member 12 to cover exposed surfaces of the three-dimensional knitted fabrics 122, 122 functioning as the natural oscillators. Between one of the three-dimensional knitted fabrics 122 and the film 123, a microphone sensor 14 which detects the vibration (sound) ascribable to the dorsal body surface pulse wave is disposed. It should be noted that the sensor is not limited to the microphone sensor 14 but may be any other sensor capable of detecting the dorsal body surface pulse wave which is weak vibration (sound). Further, as required, sensors may be disposed so as to correspond to the two three-dimensional knitted fabrics 122, 122 respectively. The third layer member 13 is stacked on a side opposite to the first layer member 11 with the second layer member 12 therebetween and reduces an external vibration input. The third layer member 13 preferably has a function of damping external vibration with high frequencies over 100 Hz. The third layer member 13 is preferably formed of a three-dimensional knitted fabric similarly to the first layer member 11 in order to have such a filtering function.

Incidentally, it is possible to impart necessary vibration damping performance to the three-dimensional knitted fabric by adjusting the mesh density of its ground kitted fabric, the thickness and material of its ground yarns, the arrangement density of its connecting yarns, the thickness and material of the connecting yarns, and so on. Further, the three-dimensional knitted fabric used as the third layer member 13 has a higher arrangement density of the coupling yarns than that of any of the three-dimensional knitted fabric forming the first layer member 11 and the three-dimensional knitted fabrics 122 functioning as the natural oscillators of the second layer member 12, thereby making vibration with a predetermined high frequency or higher difficult to transmit.

The biological signal detection unit 10 includes the first layer member 11, the second layer member 12, and the third layer member 13 as described above, and since it detects the biological signal propagated through the dorsal body surface, in particular, the dorsal body surface pulse wave containing the information on the in vivo vibration ascribable to the flowout of blood to the aorta accompanying the left ventricular expansion and the left ventricular contraction, it is preferably disposed in the aforesaid chair, bed, or the like at a position corresponding to a range from a height corresponding to the clavicle to a height corresponding to the xiphisternum. This is based on the fact that detection sensitivity in this range was high when the present inventor variously changed the attachment position of the biological signal detection unit 10. However, according to the study report in "An Optimal Spot-Electrodes Array for Voltage Pick-up Determined from the Measurement of Transthoracic Electrical Impedance Change Following Cardiac Ejection", Medical and Biological Engineering, vol. 46 No. 6 (December, 2008), in a case where electrodes are arrayed on a thorax front surface in the measurement of a cardiac output (co) using an electrical impedance method, in the range corresponding to the clavicle to the xiphisternum, an influence of a blood volume change between the atrium and the ventricle is large and an arterial blood volume change is not captured sufficiently, and the electrodes are desirably arrayed at the clavicle level and the xiphisternum level, but on the other hand, it is shown as data that, in a case where the electrodes are arrayed on the dorsal part, between the clavicle-corresponding position and the xiphisternum-corresponding position, as the electrodes are shifted from one of these positions to the other, the arterial blood volume varies at a constant rate and the blood volume between the atrium and the ventricle also varies at a constant rate. This can be said as indirect back-up indicating that making the biological signal detection unit 10 in contact with the range between the clavicle-corresponding position and the xiphisternum-corresponding position on the dorsal part enables the high-sensitivity capturing of, especially, both a blood volume change in the left ventricular diastole and an aortic blood volume change at the time of the aortic blood ejection due to the contraction of the left ventricle.

Figure 2:
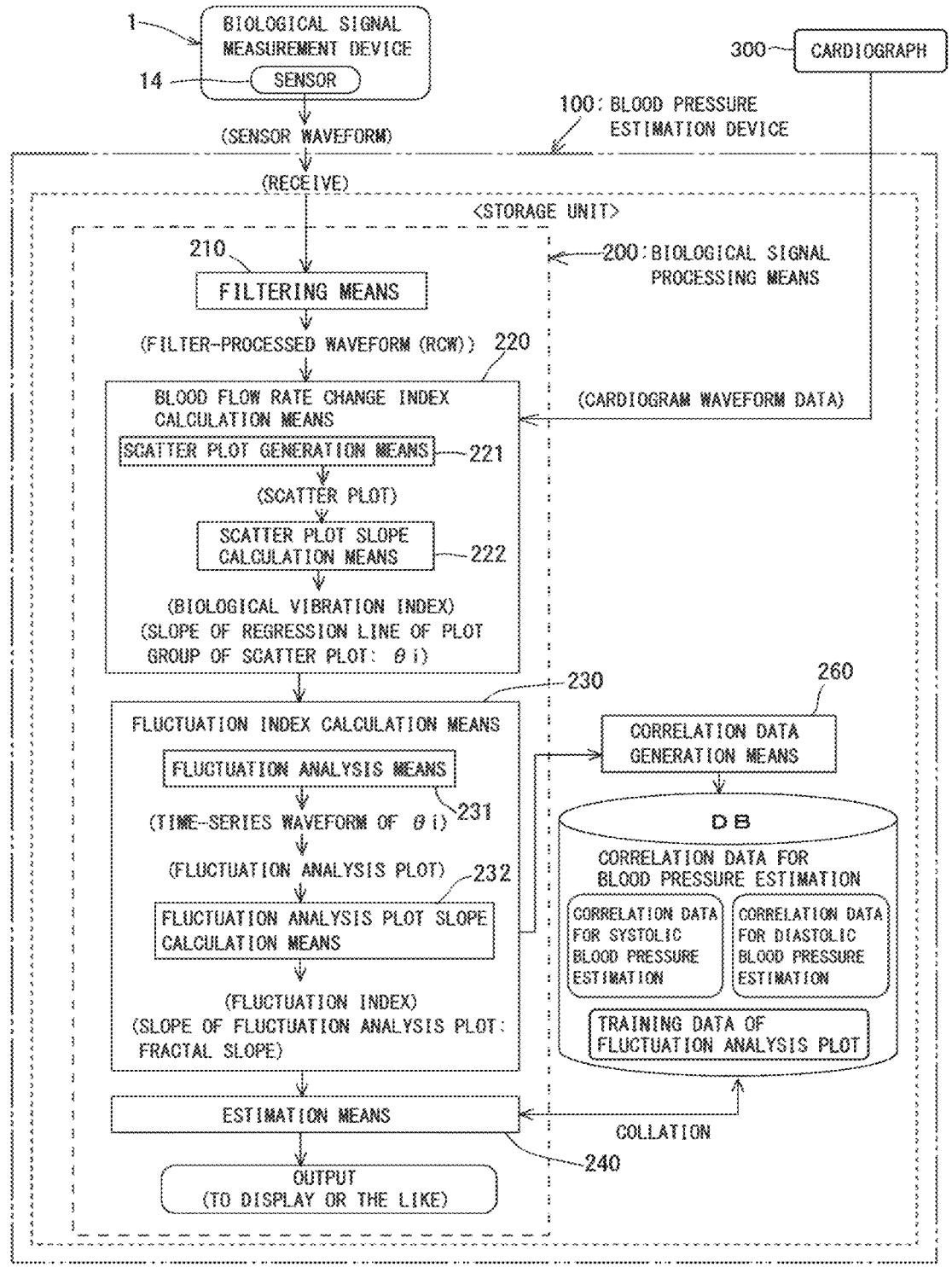
FIG. 2 is a diagram schematically illustrating the configuration of a blood pressure estimation device according to the embodiment of the present invention.

Next, the configuration of a blood pressure estimation device 100 of this embodiment will be described based on FIG. 2. The blood pressure estimation device 100 includes a biological signal processing means 200. The blood pressure estimation device 100 is constituted by a computer (including a personal computer, a microcomputer incorporated in equipment, and so on), and a computer program causing the computer to execute a biological signal processing procedure functioning as the biological signal processing means 200 is stored in a storage unit (including not only a storage medium such as a hard disk built in the computer (biological signal measurement device 100) but also various removable storage media, a storage medium of another computer connected by a communication means, and so on). Further, the computer program functioning as the biological signal processing means functions as a filtering means 210, a blood flow rate change index calculation means 220, a fluctuation index calculation means 230, and an estimation means 240 and causes the computer to execute a filtering procedure, a blood flow rate change index calculation procedure, a fluctuation index calculation procedure, and an estimation procedure. Further, it can be implemented by an electronic circuit having one storage circuit or more in which the computer program implementing the filtering procedure, the blood flow rate change index calculation procedure, the fluctuation index calculation procedure, and the estimation procedure is incorporated.

Further, the computer program can be provided in a state of being stored in a storage medium. The storage medium storing the computer program may be a non-transitory storage medium. The non-transitory storage medium is not limited, and examples thereof are storage media such as a flexible disk, a hard disk, CD-ROM, MO (magneto-optical disk), DVD-ROM, and a memory card. Further, the computer program may be transmitted to the computer through a communication line to be installed therein.

Figure 3:
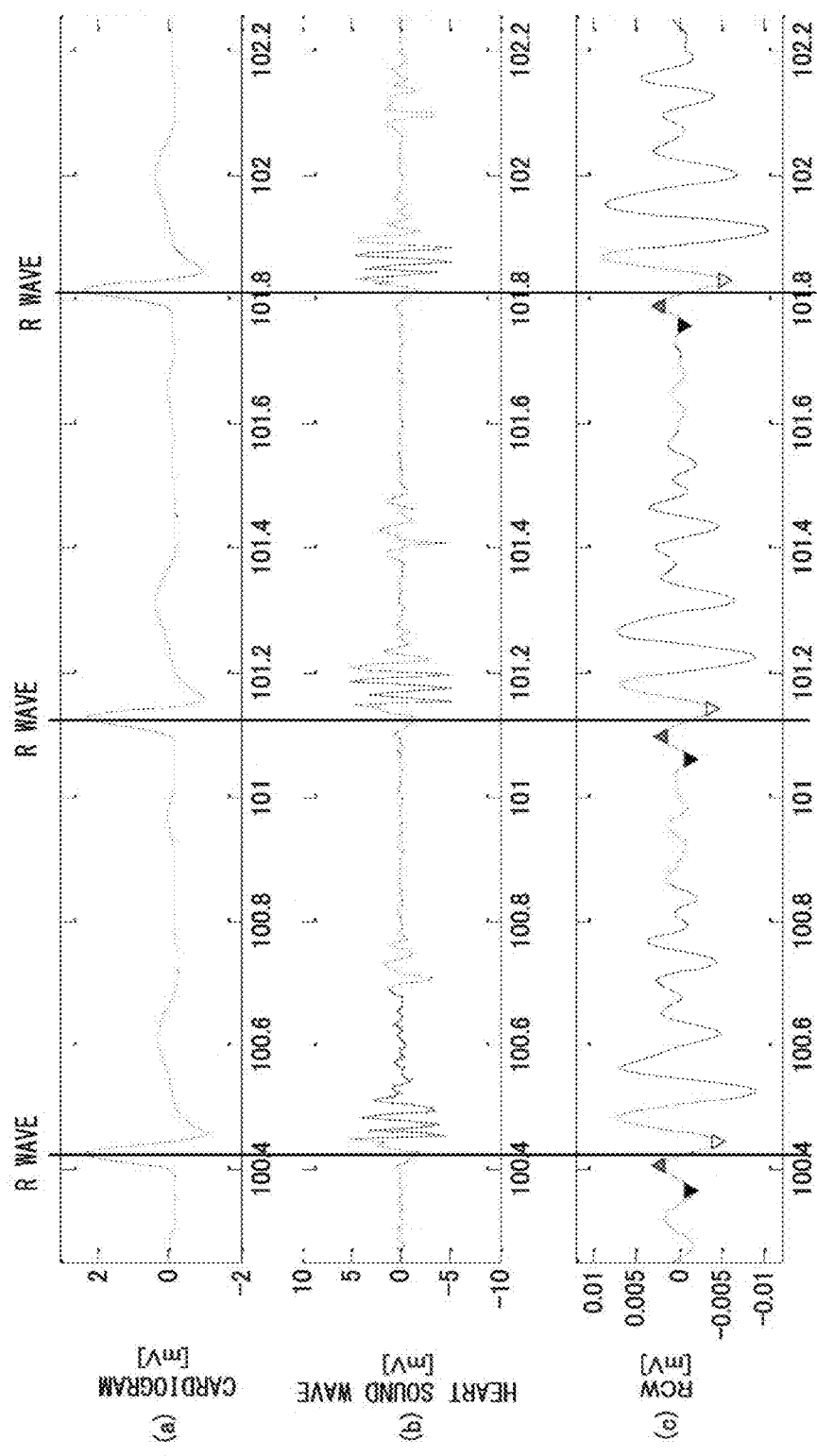
FIG. 3(a) is a chart illustrating a cardiogram waveform.
FIG. 3(b) is a chart illustrating a heart sound wave.
FIG. 3(c) is a chart illustrating a filter-processed waveform (RCW) resulting from the filtering of a time-series waveform of a biological signal obtained from the aforesaid biological signal measurement device of the embodiment.

The filtering means 210 filters a time-series waveform of the biological signal obtained from the sensor 14 incorporated in the biological signal detection unit 10 of the biological signal measurement device 1 (a waveform which is a carrier wave having biological information thereon and emphasized by a resonance phenomenon or the like in the second layer member 12 of the biological signal detection unit 10 (hereinafter, "sensor waveform")). The filtering means 210 is a means which passes the sensor waveform through a band-pass filter whose center frequency is, for example, near 20 Hz, preferably a band-pass filter whose frequency band is 10 to 30 Hz, and more preferably, further has a means which passes it through 50 Hz- and 35 Hz-notch filters to remove high-frequency components, and as a result of these filterings, the sensor waveform is converted to a filter-processed waveform of 10 to 30 Hz (the waveform in FIG. 3(c) (hereinafter, referred to as "RCW")). A standard range of heart rate is about 1 to 1.5 Hz, and as is seen from FIG. 3(c), in RCW, waveform components with a relatively large total amplitude appear at an about one-second cycle, and thus a cardiac cycle is manifested. This is apparent from the comparison between the cardiogram waveform in FIG. 3(a) and the phonocardiogram waveform in FIG. 3(b). However, RCW includes not only the cardiac-cycle rhythm but also energy of the in vivo vibration (sound) accompanying a blood flow rate change.

The blood flow rate change index calculation means 220 is a means which finds an index regarding the in vivo vibration ascribable to a blood flow rate change in the period from the ventricular filling period to the isovolumetric systole, by using waveform components in a range of the time-series waveform from the ventricular filling period to the isovolumetric systole, in RCW. As illustrated in FIG. 2, the blood flow rate change index calculation means 220 includes a scatter plot generation means (scatter plot slope generation circuit) 221 and a scatter plot slope calculation means (scatter plot slope calculation circuit) 222.

Figure 4:
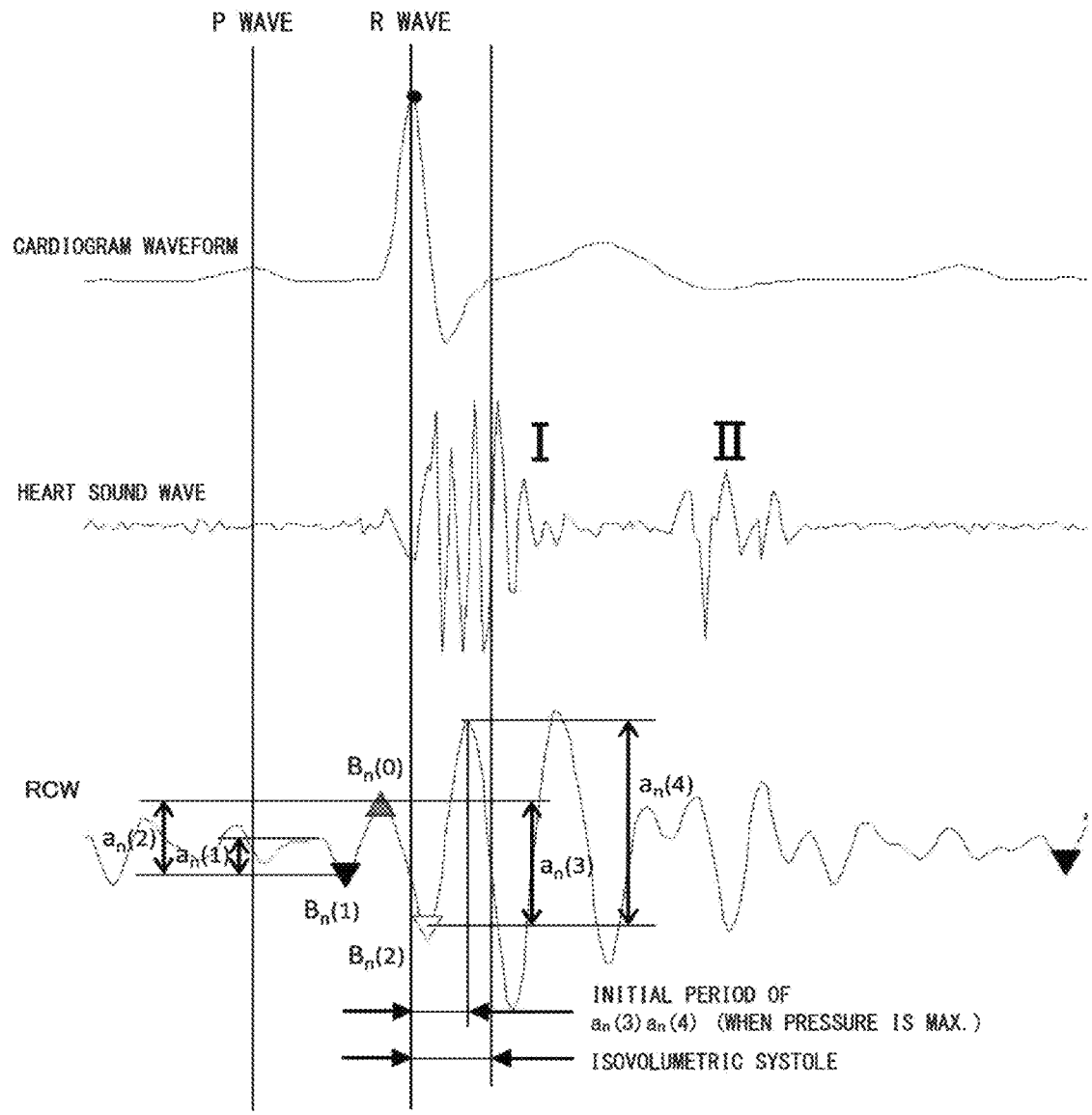
FIG. 4 is an enlarged chart of the cardiogram waveform, the heart sound wave, and the filter-processed waveform (RCW) which are illustrated in FIGS. 3 in a predetermined time zone.

The scatter plot generation means 221 specifies the aforesaid two waveform components in RCW and generates a scatter plot by using total amplitudes ($a_n(i)$, $a_n(i+1)$) of the two waveform components. The atrial contraction in the ventricular filing period lasts about 0.2 seconds before the atrioventricular valve closes (for example, about 0.17 seconds in a case where an average duration of one cardiac cycle of a person at rest is about 0.9 seconds (67 heart rate)). The waveform components during this period in RCW are used. The atrioventricular valve closes immediately after the R wave of the cardiogram waveform illustrated in FIG. 3(a), and at the timing of the R wave, the shift from the atrial contraction to the isovolumetric systole occurs, and therefore, the waveform components are selected based on the timing of the R wave in the cardiogram. FIG. 4 is an enlarged chart of a range of about 101 seconds to about 101.8 seconds in FIGS. 3(a) to (c). As illustrated in FIG. 4, an extreme point $B_n(0)$ that is immediately before the cardiogram R wave and immediately before the closure of the atrioventricular valve is first found. Next, let an extreme point that is immediately before the extreme point $B_n(0)$ be $B_n(1)$, and based on $B_n(1)$ as a reference, let an amplitude along the vertical axis from a lower-side extreme point up to an upper-side extreme point (that is, a total amplitude (p-p)) of an immediately preceding waveform component be "$a_n(1)$", and let a total amplitude of an immediately subsequent waveform component be "$a_n(2)$" The waveform components with the total amplitudes: $a_n(1)$, $a_n(2)$ specified here are within a range of 0.1 seconds immediately before the R wave, and the total amplitudes of the two waveform components reflect a blood flow rate change at the time of atrial contraction.

Further, let an extreme point immediately after the R wave, that is, an extreme point immediately after the extreme point $B_n(0)$ be $B_n(2)$, and based on the extreme point $B_n(2)$ as a reference, let a total amplitude of an immediately preceding waveform component be "$a_n(2)$", and let an immediately subsequent total amplitude be "$a_n(3)$". These are waveform components immediately before and immediately after the cardiogram R wave and reflect a blood flow rate change at the time of the shift from the ventricular filling period to the isovolumetric systole.

Figure 5:
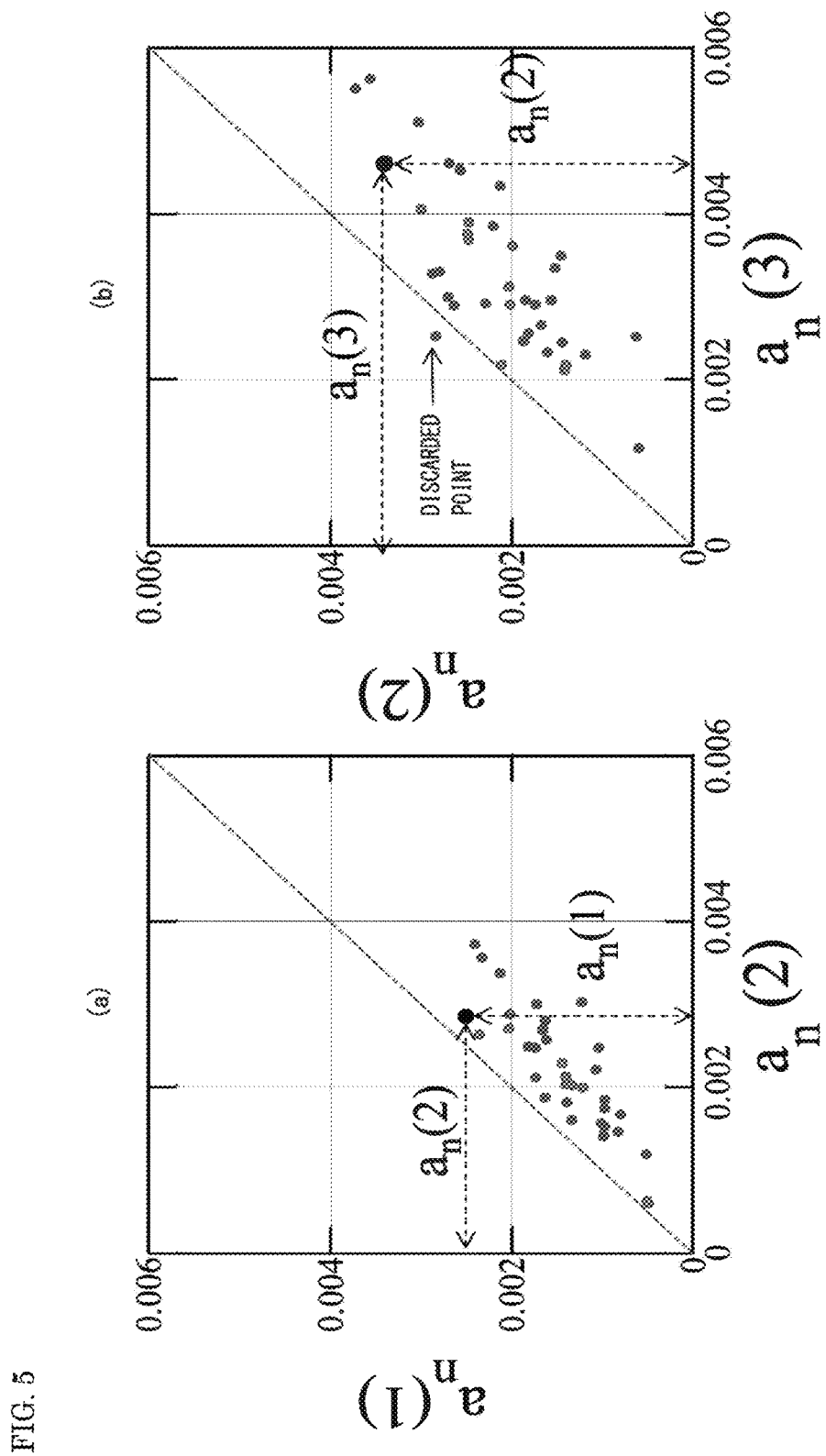
FIG. 5(a) is a scatter plot regarding waveform components reflecting a blood flow rate change at the time of atrial contraction.
FIG. 5(b) is a scatter plot regarding waveform components immediately before and immediately after the closure of the atrioventricular valve, reflecting a blood flow rate change at the time of the shift from a ventricular filling period to the isovolumetric systole.

Next, the scatter plot generation means 221 plots values of thus found total amplitudes ($a_n(i)$, $a_n(i+1)$) of the two adjacent waveform components, on a coordinate system in which one of the values is taken on the vertical axis and the other value is taken on the horizontal axis, thereby generating a scatter plot (Lorenz plot diagram) (see FIG. 5). Points plotted on the scatter plot each represent a ratio of the total amplitudes of the two waveform components.

By using the Lorenz plot method, it is possible to find a change amount of blood flowing during $\Delta t$. Specifically, atrial systolic performance gives kinetic energy to the blood, and a vibration system of the blood becomes free vibration that goes through amplification. Two kinds of damping, viscous damping and solid friction, usually act on the free vibration system, but the use of the Lorenz plot method makes it possible to find regularity in a blood flow rate presenting irregular fluctuation.

As described above, to specify the two waveform components used for the generation of the scatter plot, it is necessary to specify the R wave appearing in the cardiogram waveform immediately before the atrioventricular valve closes. In this embodiment, as illustrated in FIG. 2, the blood pressure estimation device 100 receives cardiogram waveform data from a cardiograph 300, and its information is used in the scatter plot generation means 221 of the blood flow rate change index calculation means 220 as described above. It should be noted that the kind of the cardiograph 300 is not limited at all as long as the R wave timing can be specified. Therefore, in this embodiment, data are collected by putting electrodes of the cardiograph 300 on the chest of the subject as well as disposing the biological signal detection unit 10 of the biological signal measurement device 1 on the dorsal part of a subject.

FIG. 5(a) is a scatter plot (Lorenz plot diagram) resulting from the plotting of thus found total amplitudes $a_n(1)$, $a_n(2)$ of the two waveform components reflecting the blood flow rate change at the time of the atrial contraction, and FIG. 5(b) is a scatter plot resulting from the plotting of the total amplitudes $a_n(2)$, $a_n(3)$ of the two waveform components reflecting the blood flow rate change at the time of the shift from the ventricular filling period to the isovolumetric systole, which is immediately after the appearance of the R wave. In both of them, data for thirty seconds of RCW are plotted on one coordinate system (for example, about thirty points are plotted in a case where heart rate is about 60/minute). Regarding RCW, the scatter plot generation means 221 finds such scatter plots in a time-series manner, and at this time, a calculation time width in RCW is slid with 90% overlap, for instance. Consequently, the scatter plot representing the ratio of the total amplitudes is generated at three-second intervals in this example. It should be noted that the time width and the overlap rate of the slide calculation are only examples and are not limited to the above. However, if the time width is set too long and the overlap rate is set too low, accuracy in capturing the state of the atrial contraction lowers, and therefore, it is preferable that the time width is set within a range of about ten to sixty seconds, and the overlap rate is set within a range of about 70 to 95%.

Figure 6:
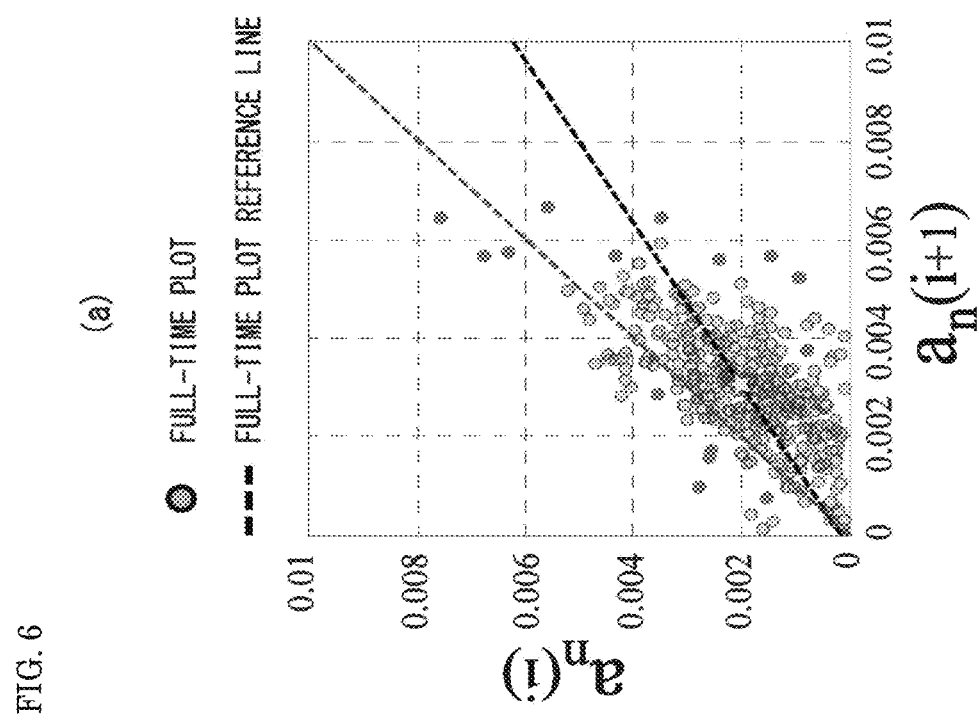
FIGS. 6(a), (b) are explanatory charts of a function of a scatter plot slope calculation means.

Regarding the plot group plotted on each of the scatter plots, the scatter plot slope calculation means 222 draws a regression line A by the least squares method and further finds a slope of the regression line A. Incidentally, as this slope, a slope relative to the horizontal axis or the vertical axis can be used as it is, but as illustrated in FIG. 6(b), a slope relative to a given reference line (full-time plot reference line) (angle between the full-time plot reference line and the 30-second regression line A) is preferably used as the slope ($\theta i$) output from the scatter plot slope calculation means 222. Further, since the slope tan° of the regression line A may be regarded as approximating θ (degree), a time-series waveform of fluctuation of θ (degree) is used for the calculation in this embodiment.

The full-time plot reference line is drawn by finding the ratio of the total amplitudes in a period (for example, the full measurement time) that is several times or more as long as the time width which is set when each of the aforesaid scatter plots is generated regarding RCW and drawing a line on a scatter plot regarding this long time period. Specifically, as illustrated in FIG. 6(a), for example, out of data in the full measurement time of 360 seconds, data whose appearance frequency is low (for example, 20% or less) is discarded by the box-counting method, and a line with the absolute maximum length starting from a point where plots with a small total amplitude waveform gather (lower end of the plot group) and passing the barycenter of the plots is the full-time plot reference line. The barycenter of the plots is at average values of the X coordinate ($a_n(i+1)$) and the Y coordinate ($a_n(i)$).

The fluctuation index calculation means 230 is a means which finds a time-series waveform of the index (blood flow rate change index) regarding the vibration occurring in the human body which index is found by the scatter plot slope calculation means 222 of the blood flow rate change index calculation means 220 and finds an index regarding fluctuation of this time-series waveform. As illustrated in FIG. 2, the fluctuation index calculation means 230 includes a fluctuation analysis means 231 and a fluctuation analysis plot slope calculation means 232.

Figure 7:
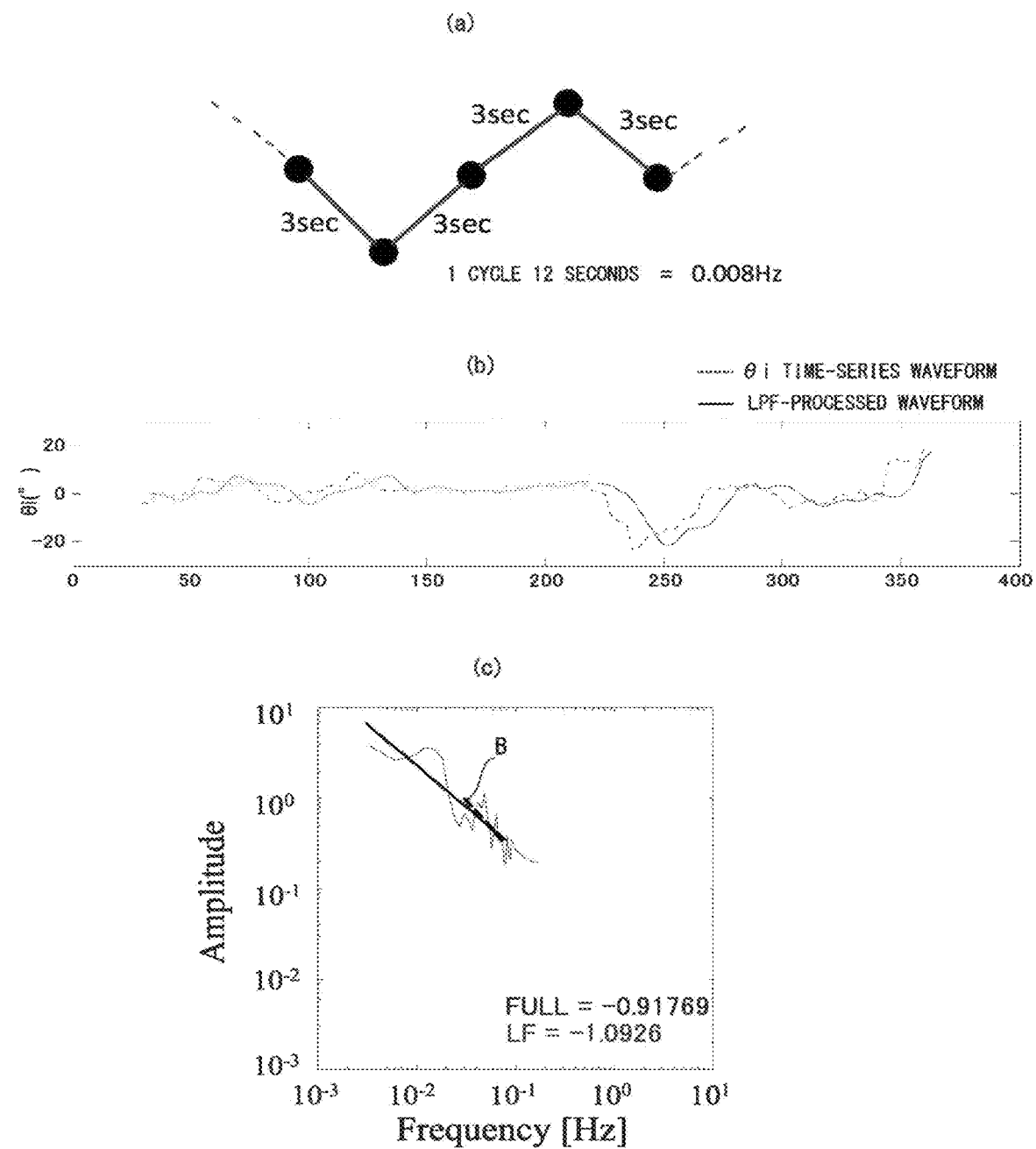
FIGS. 7(a) to (c) are explanatory charts of a function of a fluctuation analysis means.

The fluctuation analysis means 231 first plots values (blood flow rate change index) of the slope ($\theta i$) of the regression line of the plot group found by the scatter plot slope calculation means 222, in a time-series manner. In the above-described example, since the value (blood flow rate change index) of the slope ($\theta i$) of the regression line of the plot group is found at three-second intervals, the value of the slope ($\theta i$) of the regression line is plotted at three-second intervals as illustrated in FIG. 7(a), and a time-series waveform illustrated in FIG. 7(b) is newly created. Note that, in FIG. 7(b), "$\theta i$ time-series waveform" represents a time-series waveform resulting from the plotting of the values of the slope ($\theta i$) of the regression line as they are (this time-series waveform may be a time-series waveform re-drawn with the average value of all the values being set as a zero point), and "LPF-processed waveform" represents a time-series waveform obtained after the "$\theta i$ time-series waveform" is passed through a 0.08 Hz low-pass filter. In the above-described example, since the plotting is performed once per three seconds, components with high frequencies exceeding 0.08 Hz are considered as low in reliability. The time-series waveform of the value (blood flow rate change index) of the slope ($\theta i$) of the regression line of the plot group has fluctuation for responding to a change from a certain state to a subsequent state. Therefore, the fluctuation analysis means 231 performs frequency analysis (FFT) of the time-series waveform of the blood flow rate change index and represents the frequency analysis result on a power spectrum density-frequency log-log graph. Incidentally, as the time-series waveform of the value (blood flow rate change index) of the slope ($\theta i$) of the regression line which is a target of the frequency analysis, the "LPF-processed waveform" in FIG. 7(b) is preferably used rather than the "$\theta i$ time-series waveform". This frequency analysis shows which frequency governs the fluctuation (see FIG. 7(c)). In this specification, the result of this frequency analysis is referred to as "fluctuation analysis plot".

The fluctuation analysis plot slope calculation means 232 finds a regression line B of the fluctuation analysis plot obtained in the fluctuation analysis means 231 and calculates a slope of the regression line B of the fluctuation analysis plot (in the present application, the slope of the regression line B of the fluctuation analysis plot is called "fractal slope (FS)"). In this embodiment, the regression line B of the fluctuation analysis plot declines toward the right if the logarithmic scale of power spectrum density is taken on the vertical axis and the logarithmic scale of frequency is taken on the horizontal line as illustrated in FIG. 7(c) because a logarithm of the power spectrum density is inversely proportional to a logarithm of the frequency as a whole. For example, the slope (fractal slope) of the regression line B of the fluctuation analysis plot that declines at 45 degrees can be represented by "−1 (that is, 1/f fluctuation slope)".

As described above, the whole slope of the left cardiac blood flow rate change appears in VLF to LF bands, and in particular, in a case where sympathetic activity increases, a slope which looks different from the whole slope appears in these bands, and based on whether the slope in these bands takes a "+" value or a "−" value, it is possible to determine the presence/absence of the 131 receptor activation unique to a hypertensive. Further, the vicinity of 0.003 to 0.08 Hz is a frequency band reflecting the work of a blood-pressure regulating hormone (renin-angiotensin-aldosterone system), and 0.1 Hz vibration (periodic vibration on an excitation level of the sympathetic vasoconstrictor nerves) called a Mayer wave also has an influence on blood pressure. Considering these, the slope (fractal slope) of the regression line B of the fluctuation analysis plot which slope is a fluctuation index is preferably found in a predetermined frequency band set between the VLF band (very-low-frequency band: 0.0033 to 0.04 Hz) and the LF band (low-frequency band: 0.04 to 0.15 Hz). The upper limit value of the predetermined frequency band is preferably first set to around 0.08 Hz because, in this embodiment, the 0.08 Hz low-pass filter is applied when the time-series waveform of the blood flow rate change index is generated as described above. On the other hand, its lower limit value is preferably set to a value between 0.01 to 0.04 Hz since data with 0.01 Hz or less does not noticeably contain information on the blood flow rate change. For example, when heart rate increases, blood pressure tends to drop in some cases, and at this time, the fluctuation of the blood flow rate change may tend to appear on a lower frequency side. Therefore, the predetermined frequency band is preferably set for each subject whose blood pressure is to be estimated though it can be set uniformly to 0.03 to 0.08 Hz, for instance.

As a method of setting it for each subject whose blood pressure is to be estimated, the following method is used in this embodiment. Specifically, as will be described later, in the blood pressure estimation, the fractal slope (FS) which is the fluctuation index of the subject is collated with correlation data for blood pressure estimation. This necessitates finding, in advance, the correlation data for blood pressure estimation (correlation equation for blood pressure estimation) in which a brachial blood pressure value and the fractal slope (SF) are associated and setting it in the storage unit. Therefore, for generating the correlation data for blood pressure estimation, a frequency band appropriate for finding the fractal scope (FS) is individually set for each fluctuation analysis plot of each subject in consideration of the heart rate and so on of the subject. Then, these fluctuation analysis plots are used as training data, the fluctuation analysis plot of a subject whose blood pressure is to be estimated is collated with these pieces of training data, and training data with the highest matching degree is extracted, then by using a frequency band used in this training data in the fluctuation analysis plot of the subject whose blood pressure is to be estimated, it is possible to calculate the fractal slope (FS). The use of this method makes it possible to automatically set the predetermined frequency band for each subject after the correlation data for blood pressure estimation is generated. Incidentally, by repeating a step of accumulating newly found data as new training data and newly finding the correlation data for blood pressure estimation (correlation equation for blood pressure estimation) by including the newly found training data, it is possible to enhance blood pressure estimation accuracy.

The fractal slope (FS) as the fluctuation index which is output from the fluctuation analysis plot slope calculation means 232 is used in the blood pressure estimation in the later-described estimation means 240, and for this, it is necessary to generate correlation data of blood pressure and the fractal slope (FS) (correlation data for blood pressure estimation) in advance. Therefore, in this embodiment, the biological signal processing means 200 includes a correlation data generation means 260 which generates the correlation data for blood pressure estimation by using the fractal slope being the fluctuation index which is output from the fluctuation analysis plot slope calculation means 232 (FIG. 2). The correlation data generation means 260 executes the following procedure to generate the correlation data and stores it in the storage unit.

In the generation of the correlation data for blood pressure estimation, as the value (blood flow rate change index) of the slope (θi) of the regression line of the plot group found by the scatter plot slope calculation means 222, one obtained from the scatter plot in which the total amplitudes $a_n(1)$, $a_n(2)$ of the two waveform components reflecting the blood flow rate change at the time of the atrial contraction are plotted is adopted for the estimation of diastolic blood pressure, and one obtained from the scatter plot in which the total amplitudes $a_n(2)$, $a_n(3)$ of the two waveform components, immediately before and after the closure of the atrioventricular valve, which waveform components reflect the blood flow rate change at the time of the shift from the ventricular filling period to the isovolumetric systole are plotted is adopted for the estimation of systolic blood pressure.

Figure 8:
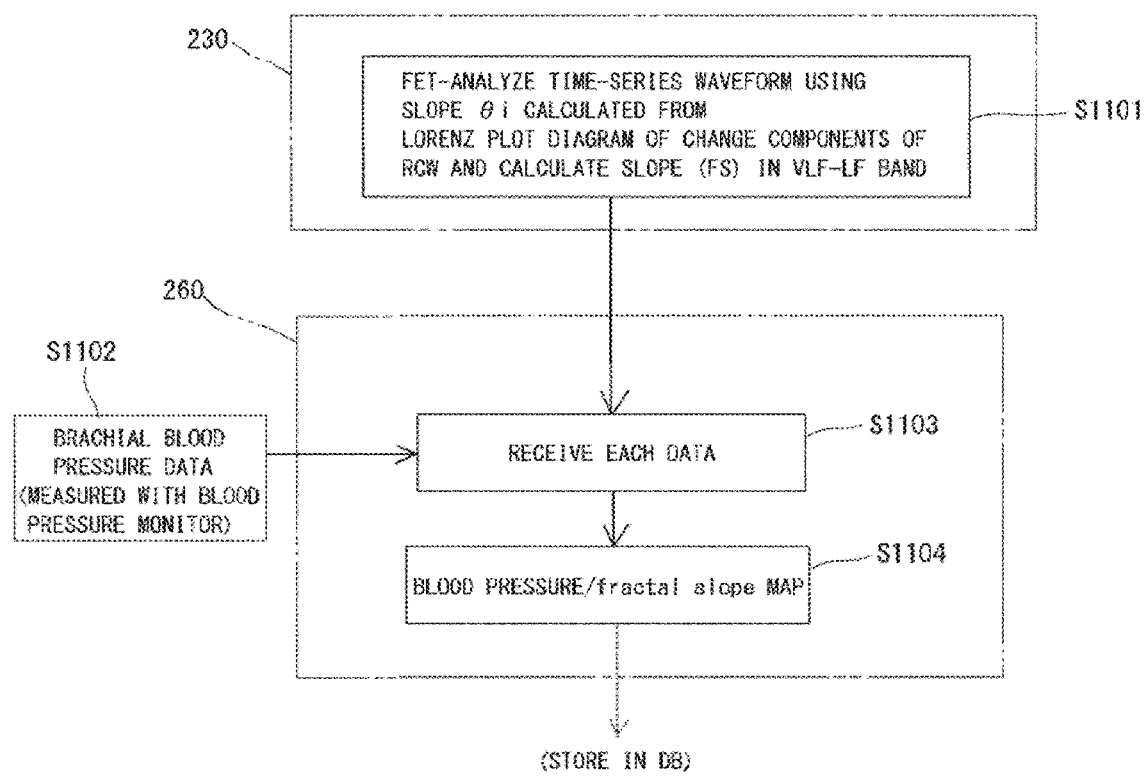
FIG. 8 is a flowchart illustrating a procedure for generating correlation data for blood pressure estimation.
Figure 9:
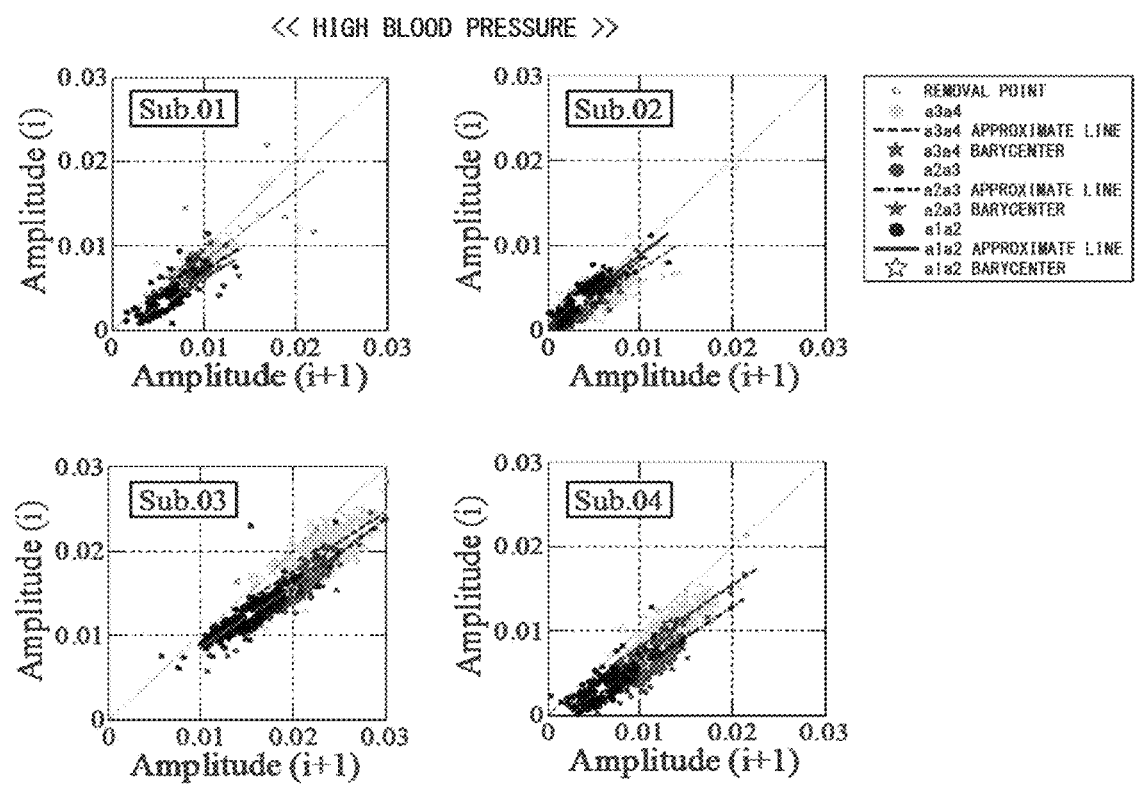
FIG. 9 illustrates charts for four subjects with high blood pressure, each showing a scatter plot and a scatter plot slope.
Figure 10:
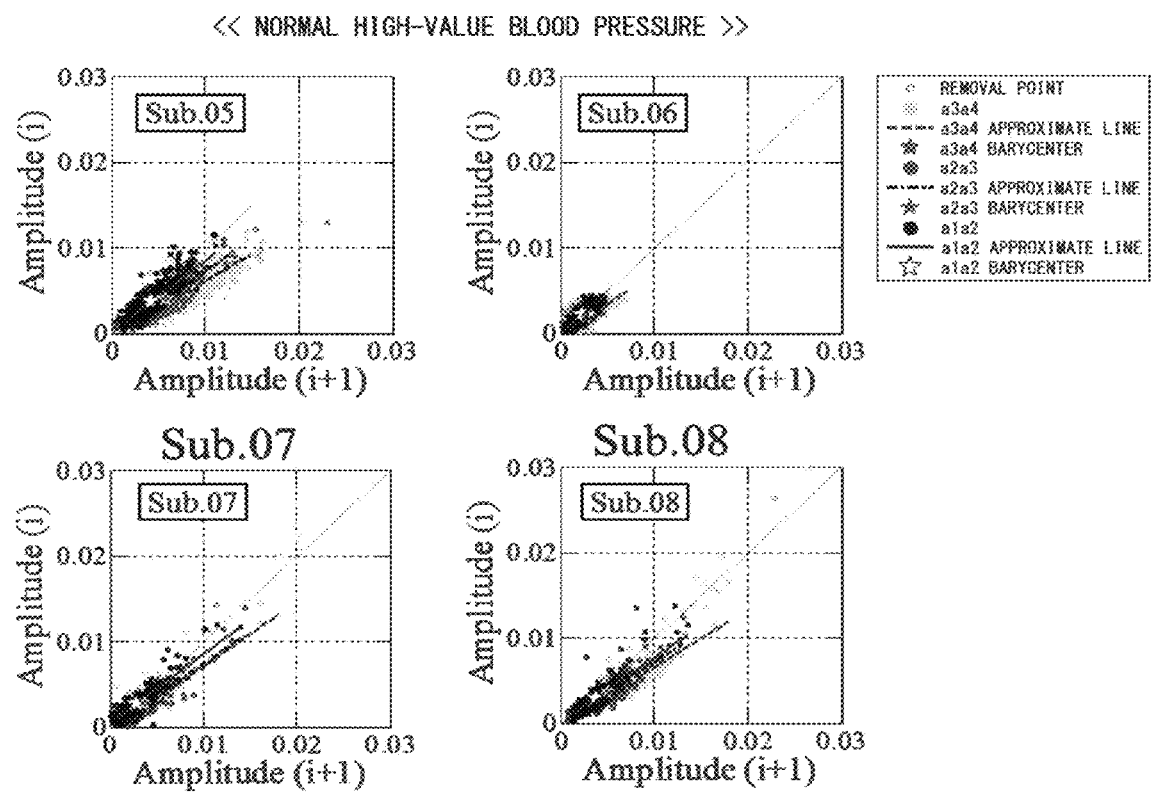
FIG. 10 illustrates charts for four subjects with normal high-value blood pressure, each showing a scatter plot and a scatter plot slope.
Figure 11:
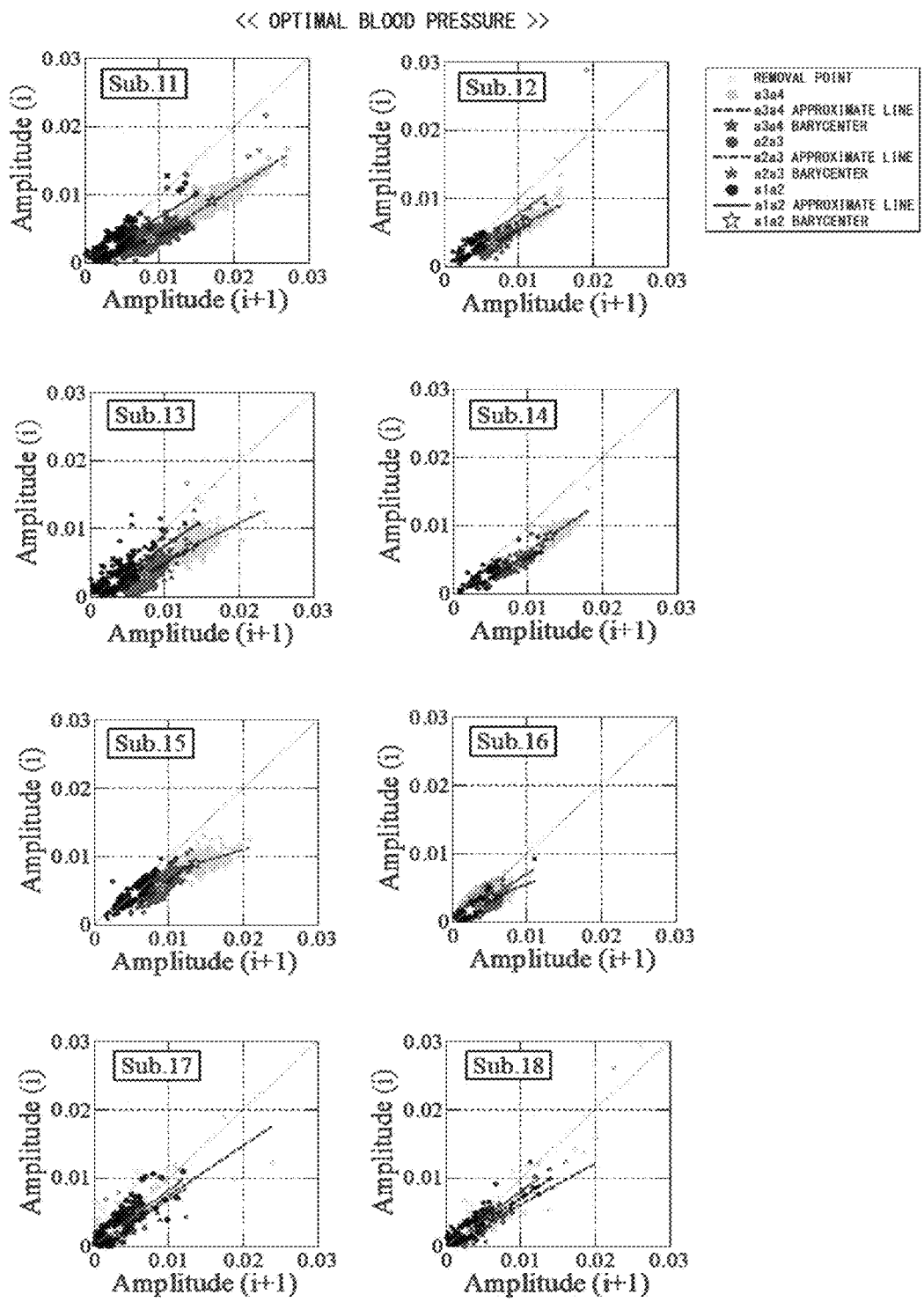
FIG. 11 illustrates charts for eight subjects with optimal blood pressure, each showing a scatter plot and a scatter plot slope.
Figure 12:
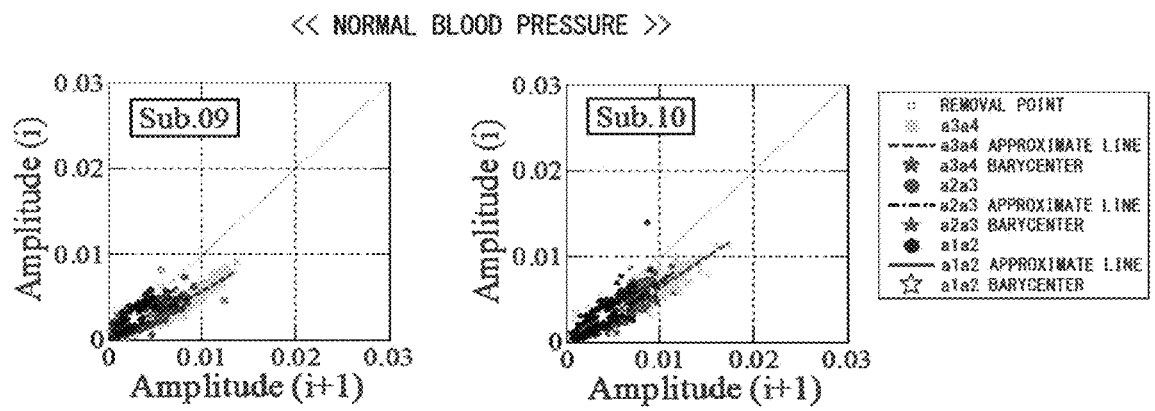
FIG. 12 illustrates charts for two subjects with normal blood pressure, each showing a scatter plot and a scatter plot slope.
Figure 13:
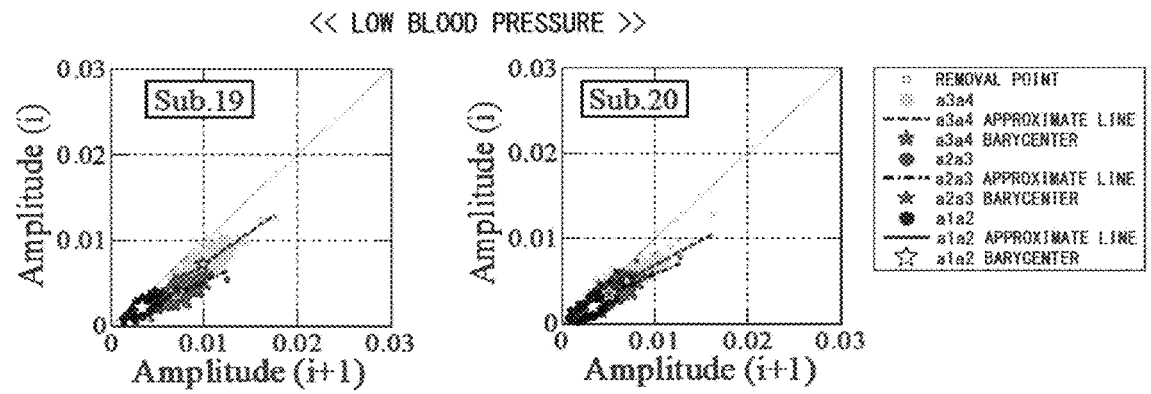
FIG. 13 illustrates charts for two subjects with low blood pressure, each showing a scatter plot and a scatter plot slope.
Figure 16:
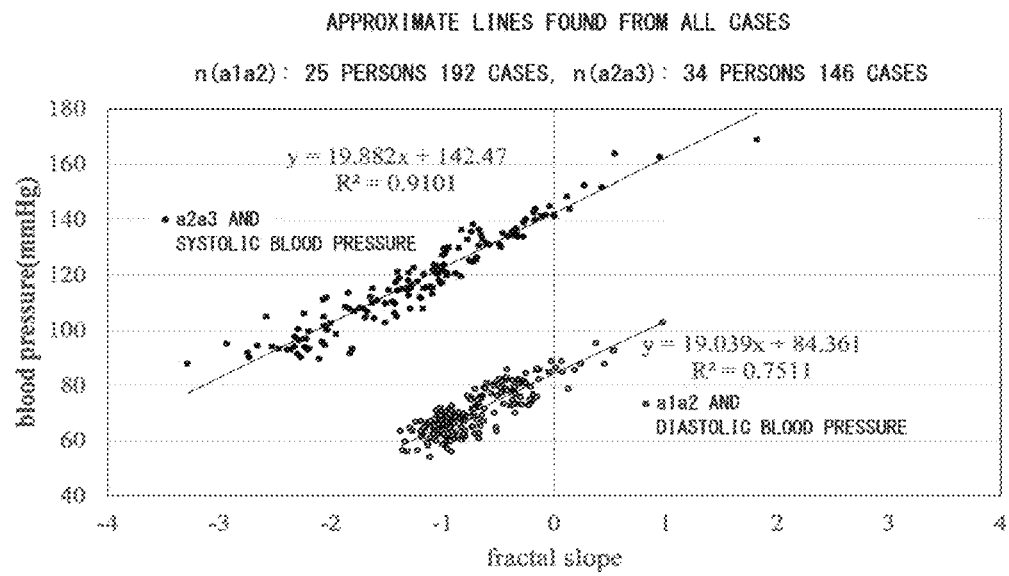
FIG. 16 is a chart illustrating an example of the correlation data for blood pressure estimation of this embodiment.
Figure 17:
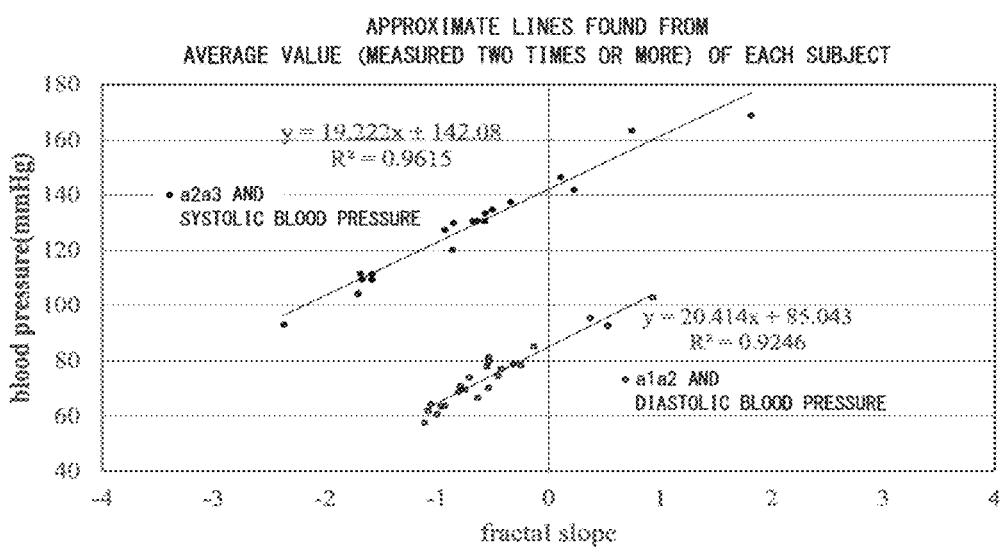
FIG. 17 is a chart illustrating an example of the correlation data for blood pressure estimation of this embodiment which is found using an average value of values of the fractal slope (FS) and an average value of brachial blood pressure values.

Then, as illustrated in FIG. 8, after the slope (fractal slope (FS)) of the regression line B is calculated by the fluctuation index calculation means 230 (S1101), the correlation data generation means 260 receives this data (S1103). Further, almost at the same timing, it also receives (S1103) data of a subject's brachial blood pressure measured with a blood pressure monitor (S1102). It should be noted that a method of measuring the brachial blood pressure is not limited, and needless to say, a blood pressure monitor of a type having a cuff to be wound around an upper part of the arm (brachial blood pressure monitor), a wrist blood pressure monitor, or the like may be used for the measurement. The correlation data for blood pressure estimation (blood pressure/fractal slope MAP) is thus generated (S1104), and this data is stored in the storage unit. FIG. 16 or FIG. 17, which will be described later, illustrates an example of the correlation data for blood pressure estimation, and both in FIG. 16 and FIG. 17, the slope (fractal slope (FS)) of the regression line B in the LF band is taken on the horizontal axis and the brachial blood pressure data is taken on the vertical axis, and two correlation lines (correlation equations) respectively representing correlation data for diastolic blood pressure estimation and correlation data for systolic blood pressure estimation are found.

The estimation means 240 estimates the blood pressure by using, as the fluctuation index, the value of the fractal slope found by the fluctuation analysis plot slope calculation means 232. Specifically, the value of the fractal slope (FS) of an evaluation subject is collated with the aforesaid correlation data for blood pressure estimation stored in the storage unit to estimate his/her blood pressure (see FIG. 2). For example, when the fractal scope (FS) that is the fluctuation index found using $a_n(1)$ (indicated simply as "a1" in the drawings and in the below) and $a_n(2)$ (indicated simply as "a2" in the drawings and in the below) is output as "−0.2", in FIG. 16, it is substituted in the equation y=19.039x+84.361, and the blood pressure is found to be about 81 mm Hg, and when FIG. 17 is used, it is substituted in the equation y=20.414x+85.043, and the blood pressure is estimated to be about 81 mm Hg. Further, when the fractal scope (FS) that is the fluctuation index found using a2 and $a_n(3)$ (indicated simply as "a3" in the drawings and in the below) is output as "−1", in FIG. 16, it is substituted in the equation y=19.813x+142.5, and the blood pressure is estimated to be about 123 mm Hg, and when FIG. 17 is used, it is substituted in the equation y=19.006x+141.93, and the blood pressure is estimated to be about 123 mm Hg. According to this embodiment, since the fractal slope (FS) using a1 and a2 and the fractal slope (FS) using a2 and a3 can both be found one after another, it is possible to continuously estimate the blood pressure of a subject in the non-constraining manner.

Here, a process of generating the correlation data for blood pressure estimation illustrated in FIG. 16 and FIG. 17 will be described using FIG. 9 to FIG. 15. First, FIG. 9 to FIG. 13 illustrate scatter plots (Lorenz plot diagrams) which are generated by the scatter plot generation means 221 of the blood flow rate change index calculation means 220 after the filtering means 210 filters dorsal body surface pulse waves of twenty representative subjects (subjects (Sub.) No. 01 to 20). Note that the dorsal body surface pulse waves collected from these subjects are those when they are at rest. In all of these, points found using a1 and a2 (indicated as "a1a2" in the notes in the drawings) and points found using a2 and a3 (indicated as "a2a3" in the notes in the drawings) are both plotted. Further, the regression lines A found by the scatter plot slope calculation means 222 regarding plot groups of "a1a2" points and "a2a3" points ("a1a2 approximate lines" and "a2a3 approximate lines" respectively) are illustrated. Then, the scatter plot slope calculation means 222 finds slopes (θ) of these a1a2 approximate lines and a2a3 approximate lines.

Note that, in the analyses in FIG. 9 to FIG. 15, the brachial blood pressure values of the subjects at rest were classified into the following blood pressure types based on the blood pressure classification in the Guidelines for Hypertension (2014) of the Japanese Society of Hypertension. First, a case where the systolic blood pressure was 140 mmHg or higher and/or the diastolic blood pressure was 90 mmHg or higher was classified as "high blood pressure", and a case where they were less than the conditions of "high blood pressure" was classified as "normal-range blood pressure". Further, regarding "normal-range blood pressure", a case where the systolic blood pressure was 130 to 139 mmHg and/or the diastolic blood pressure was 85 to 89 mmHg was classified as "normal high-value blood pressure", a case where the systolic blood pressure was 120 to 129 mmHg and/or the diastolic blood pressure was 80 to 84 mmHg was classified as "normal blood pressure", and a case where the systolic blood pressure was less than 120 mmHg and the diastolic blood pressure was less than 80 mmHg was classified as "optimal blood pressure". Regarding "low blood pressure", the standard of the World Health Organization which stipulates it as a 100 mmHg systolic blood pressure or less and a 60 mm Hg diastolic blood pressure or less is adopted since the aforesaid guideline gives no stipulation.

Next, the fluctuation analysis means 231 of the fluctuation index calculation means 230 finds time-series waveforms (see FIG. 7(b)) of the slopes (θ1) of the a1a2 approximate lines and the a2a3 approximate lines found by the scatter plot slope calculation means 222, performs frequency analysis (FFT), and finds fluctuation analysis plots which are power spectrum density-frequency log-log graphs (see FIG. 7(c)). The fluctuation analysis plot slope calculation means 232 sets a predetermined frequency band in the VLF to LF bands by referring to the heart rate and so on of each of the subjects as described above, and finds the fractal slopes (FS) which are the slopes of the regression lines B of the fluctuation analysis plots.

Figure 14:
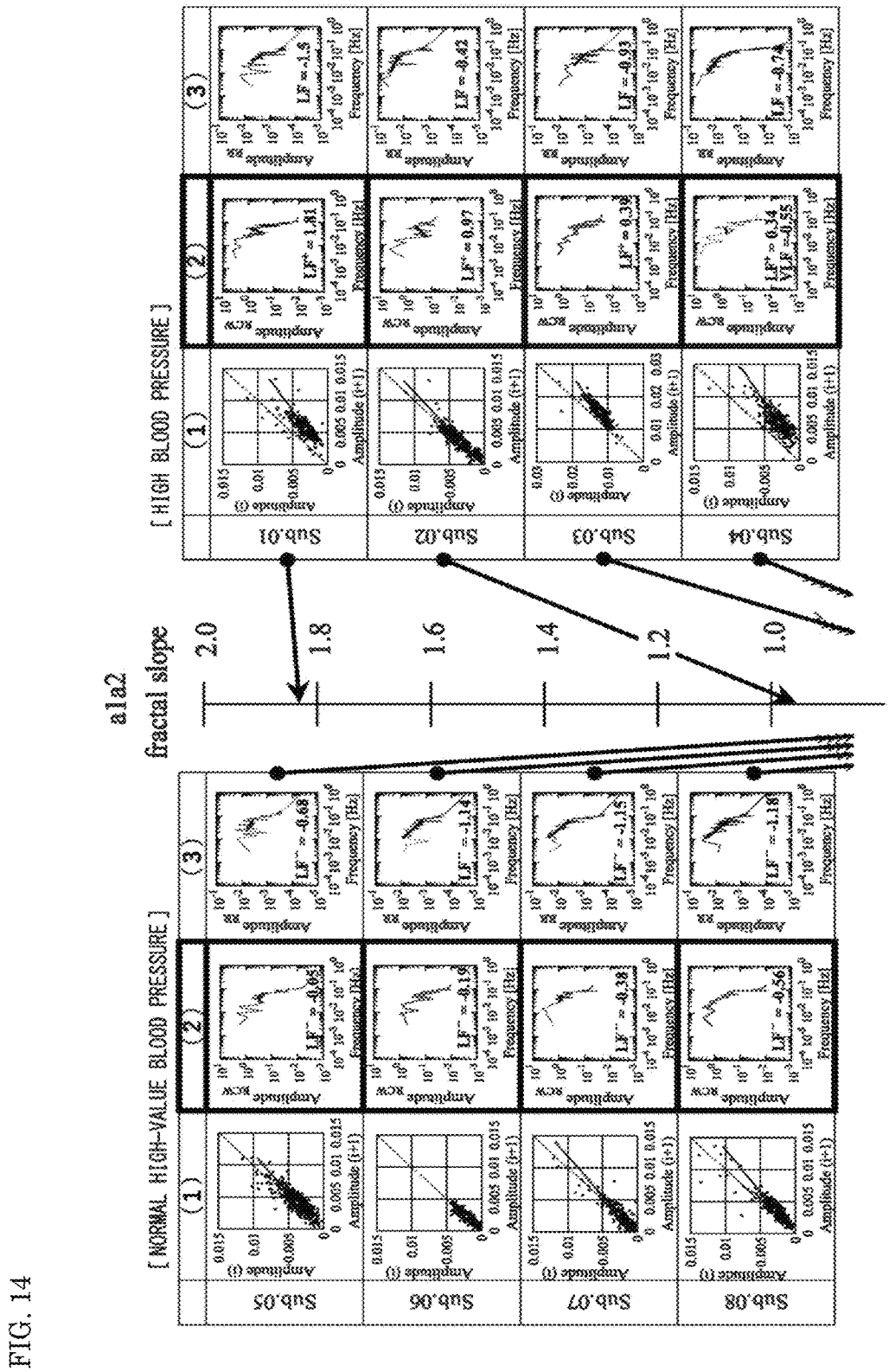
FIG. 14 is a chart in which examples of scatter plots using the waveform components $a_n(1)$, $a_n(2)$ (a1a 2) reflecting the blood flow rate change at the time of atrial contraction, scatter plot slopes, fluctuation analysis plots, and fractal slopes (FS) found therefrom are shown together.
Figure 14:
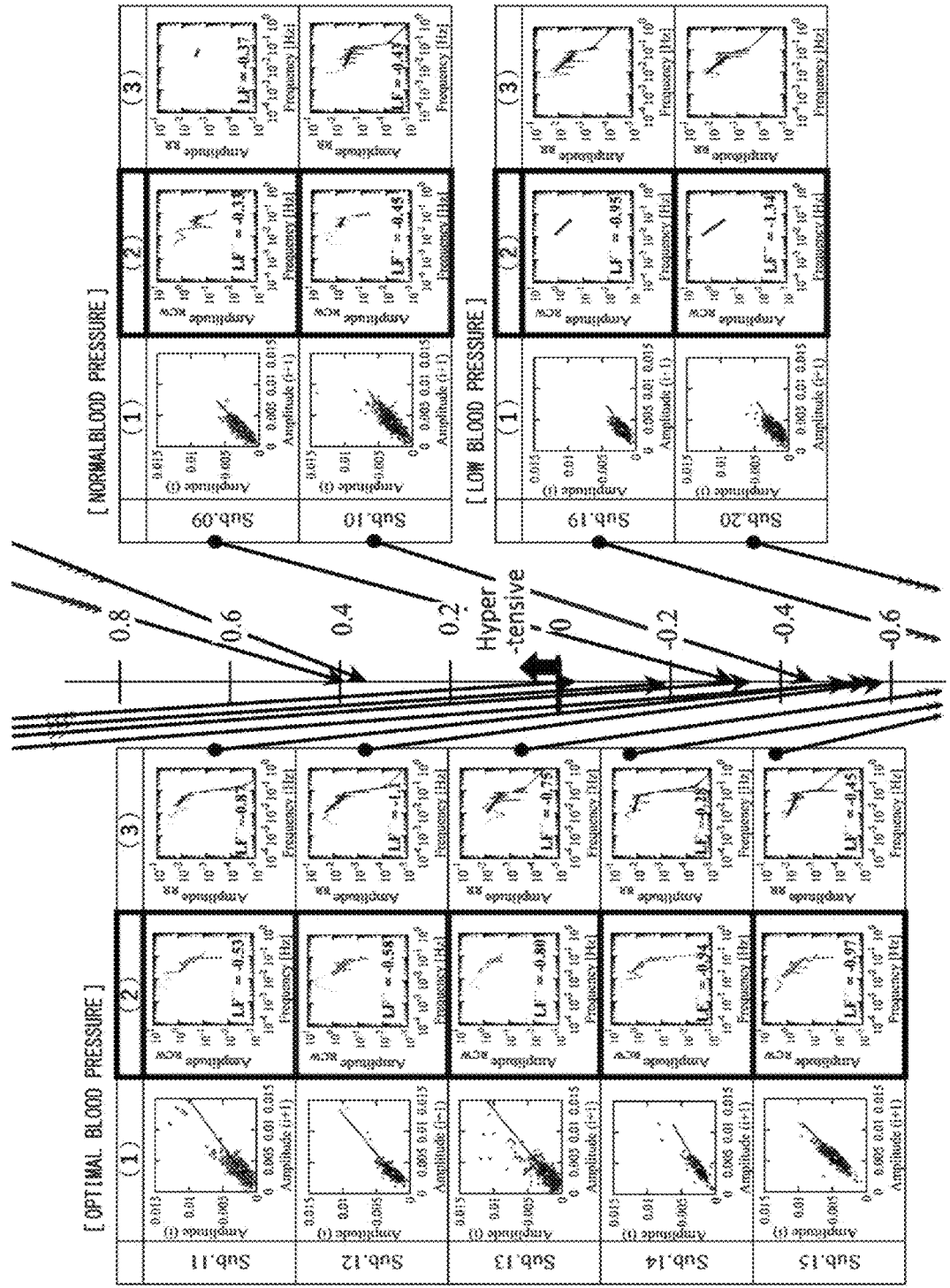
Figure 15:
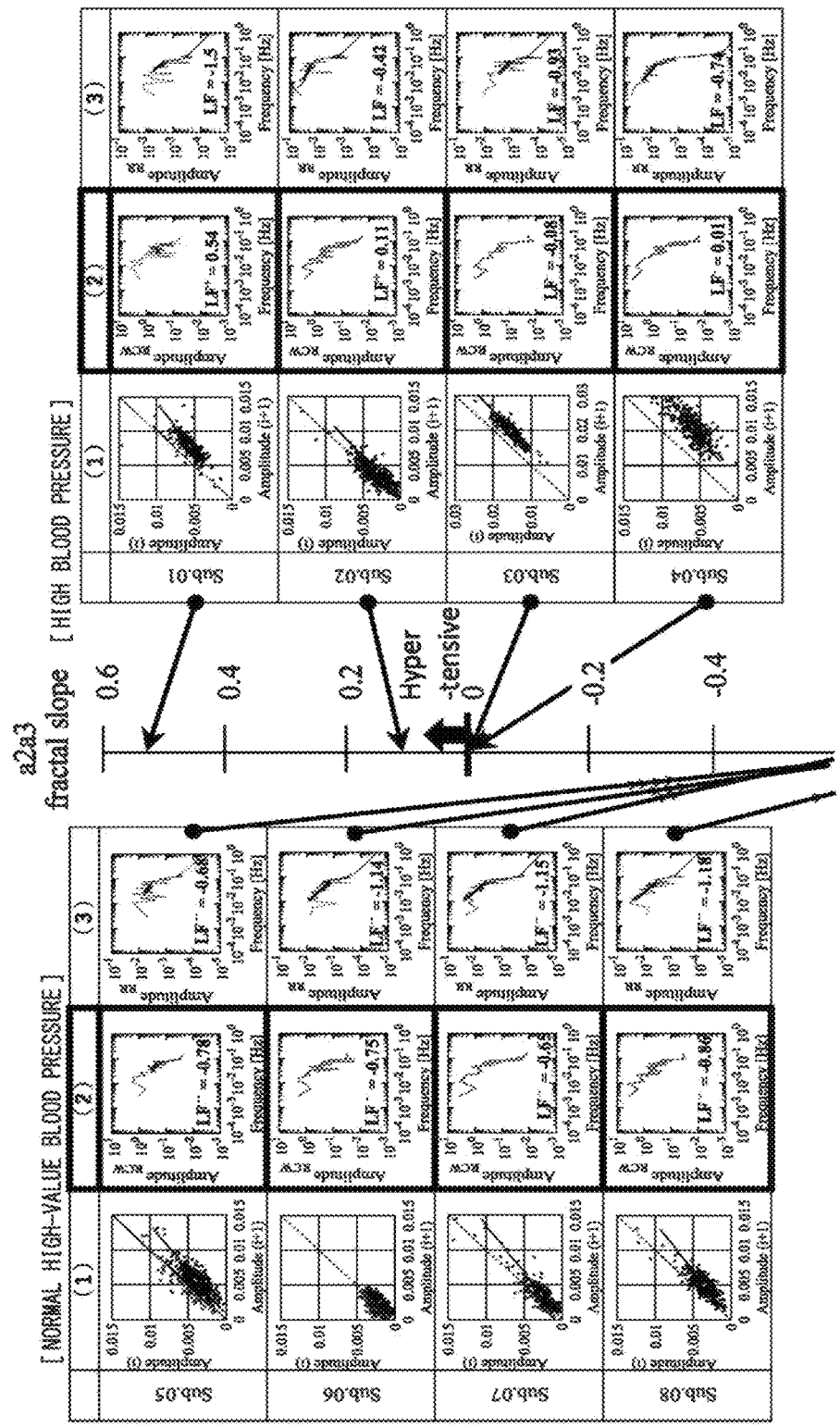
FIG. 15 is a chart in which examples of scatter plots using the waveform components $a_n(2)$, $a_n(3)$ (a2a3) reflecting the blood flow rate change at the time of the shift from the ventricular filling period to the isovolumetric systole, scatter plot slopes, fluctuation analysis plots, and fractal slopes (FS) found therefrom are shown together.
Figure 15:
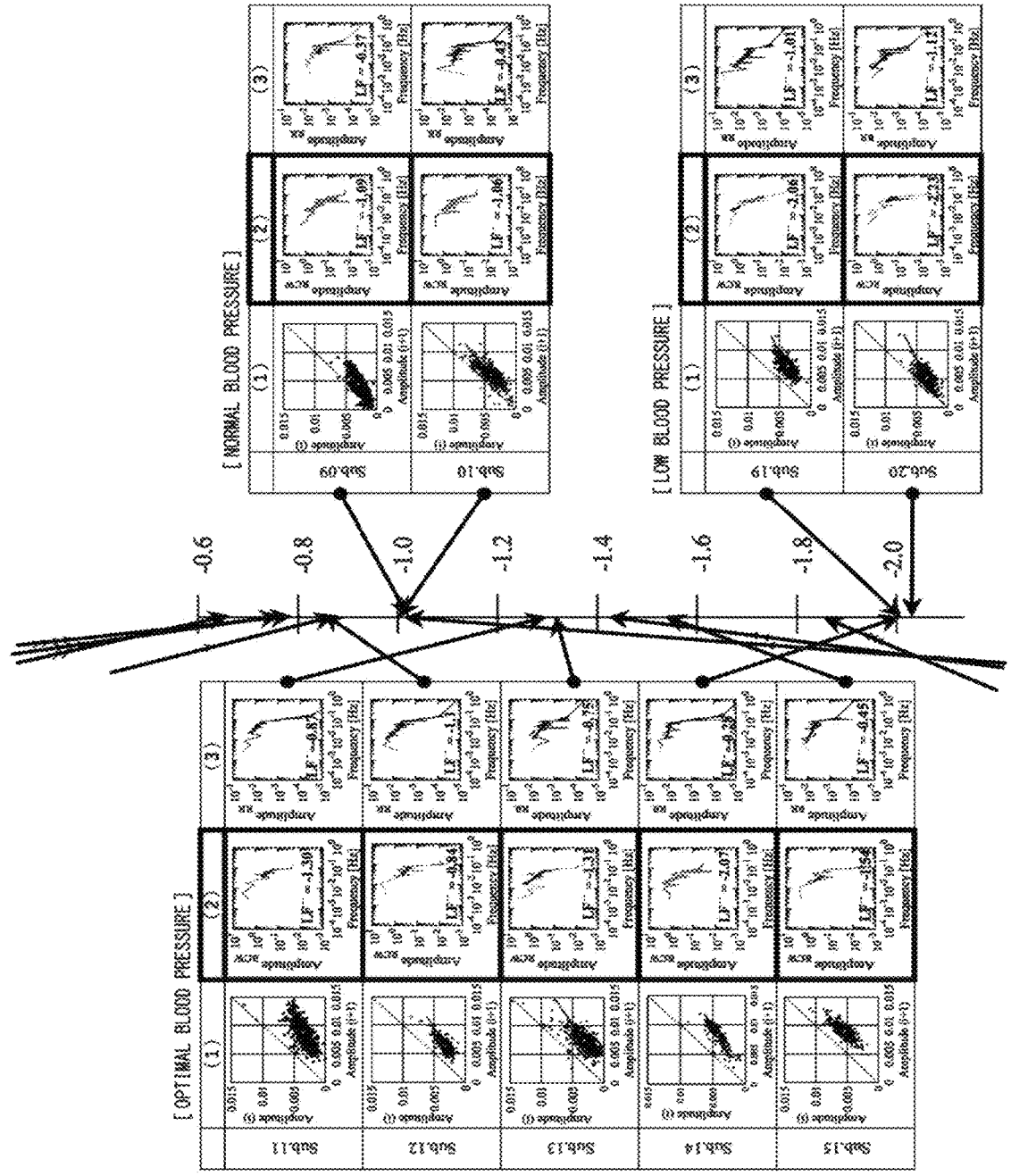

Next, the correlation data generation means 260 can obtain the fractal slopes (FS) illustrated in FIG. 14 regarding a1a2 corresponding to the diastolic blood pressure and can obtain the fractal slopes illustrated in FIG. 15 regarding a2a3 corresponding to the systolic blood pressure. In FIG. 14 and FIG. 15, the middle columns (the columns indicated as "(2)") each correspond to the aforesaid fluctuation analysis plot, in which the fractal slope (FS) found in the predetermined frequency band is found. Note that, in FIG. 14 and FIG. 15, the left columns (the columns indicated as "(1)") each illustrate a scatter plot (Lorenz plot diagram) and the right columns (the columns indicated as "(3)") each illustrate a spectrum resulting from the analysis of fluctuation of a time-series waveform of heart rate obtained from the cardiograph 300. A fractal slope of the spectrum resulting from the analysis of the fluctuation of the time-series waveform of the heart rate did not show a significant correlation with the blood pressure.

Referring to the middle columns (2), in, for example, the subject No. 05 having the blood pressure classified into the range of the normal high-value blood pressure, the a1a2-based fractal slope (FS) in FIG. 14 was "−0.05", and the a2a3-based fractal slope in FIG. 15 was "−0.78". As for the brachial blood pressure of the subject No. 05 at this time, the diastolic blood pressure was 83 and the systolic blood pressure was 133. Then, in FIG. 16, the 83 diastolic blood pressure is plotted versus the value "−0.05" of the a1a2-based fractal slope (FS), and the 133 systolic blood pressure is plotted versus the value "−0.78" of the a2a3-based fractal slope (FS).

Similarly, in the subject No. 11 having a blood pressure classified into the range of the optimal blood pressure, the a1a2-based fractal slope (FS) in FIG. 14 was "−0.53" and the a2a3-based fractal slope (FS) in FIG. 15 was "−1.30". As for the brachial blood pressure of the subject No. 11 at this time, the diastolic blood pressure was 65 and the systolic blood pressure was 108. Then, in FIG. 16, the 65 diastolic blood pressure is plotted versus the value "−0.53" of the a1a2-based fractal slope (FS) and the 108 systolic blood pressure is plotted versus the value "−1.30" of the a2a3-based fractal slope (FS).

Further, in the subject No. 01 having a blood pressure classified into the range of the high blood pressure, the a1a2-based fractal slope (FS) in FIG. 14 was "+1.81" and the a2a3-based fractal slope (FS) in FIG. 15 was "+0.54". As for the brachial blood pressure of the subject No. 01 at this time, the diastolic blood pressure was 116 and the systolic blood pressure was 164. Then, in FIG. 16, the 116 diastolic blood pressure is plotted versus the value "+1.81" of the a1a2-based fractal slope (FS), and the 164 systolic blood pressure is plotted versus the value "+0.54" of the a2a3-based fractal slope (FS).

The same processing is performed for the other subjects to plot the results in FIG. 16. As a result of such plotting, almost all the values of both the a1a2-based and a2a3-based fractal slopes (FS) of subjects classified into high blood pressure were 0 or more, and almost all the values of both the a1a2-based and a2a3-based fractal slopes (FS) of subjects with the normal-range blood pressure (normal high-value blood pressure, normal blood pressure, optimal blood pressure, low blood pressure) were 0 or less. Then, the regression line drawn on the a1a2-based plot group plotted in FIG. 16 was y=19.039x+84.361 and a coefficient of determination was 0.7511, indicating a high correlation. Further, a value of a y intercept when the value of the fractal slope (FS) was "0" was "84.361", and regarding the diastolic blood pressure, it was a value close to 90 mmHg which is a boundary between the high blood pressure and the normal-range blood pressure and was substantially the same value as 85 mmHg which is a boundary between the normal high-value blood pressure and the normal blood pressure. This regression line is the correlation data for diastolic blood pressure estimation found finally.

The regression line drawn on the a2a3-based plot group was y=19.882x+142.47 and a coefficient of determination was 0.9101, indicating a high correlation. Further, a value of a y intercept when the value of the fractal slope (FS) was "0" was "142.47", and regarding the systolic blood pressure, it was a value close to 140 mmHg which is a boundary between the high blood pressure and the normal-range blood pressure. This regression line is the correlation data for systolic blood pressure estimation found finally. Note that the data plotted in FIG. 16 are 129 data of 25 subjects for a1a2 and 146 data of 34 subjects for a2a3.

FIG. 17 is correlation data for blood pressure estimation generated using average values of the values of the fractal slopes (FS) regarding a1a2 and a2a3 and average values of the diastolic blood pressures and the systolic blood pressures which are measured with the brachial blood pressure monitor, of the subjects who are subjected to the measurement a plurality of times, out of the data plotted in FIG. 16. The regression line of the correlation data for diastolic blood pressure estimation using a1a2 was y=20.414x+85.043 and its coefficient of determination was 0.9246. The regression line of the correlation data for diastolic blood pressure estimation using a2a3 was y=19.222x+142.08 and its coefficient of determination was 0.9615. Both of these have a higher correlation than the regression lines found in FIG. 16, and in generating the correlation data for blood pressure estimation, an average value of a plurality of measurement values of each subject is preferably used.

Figure 18:
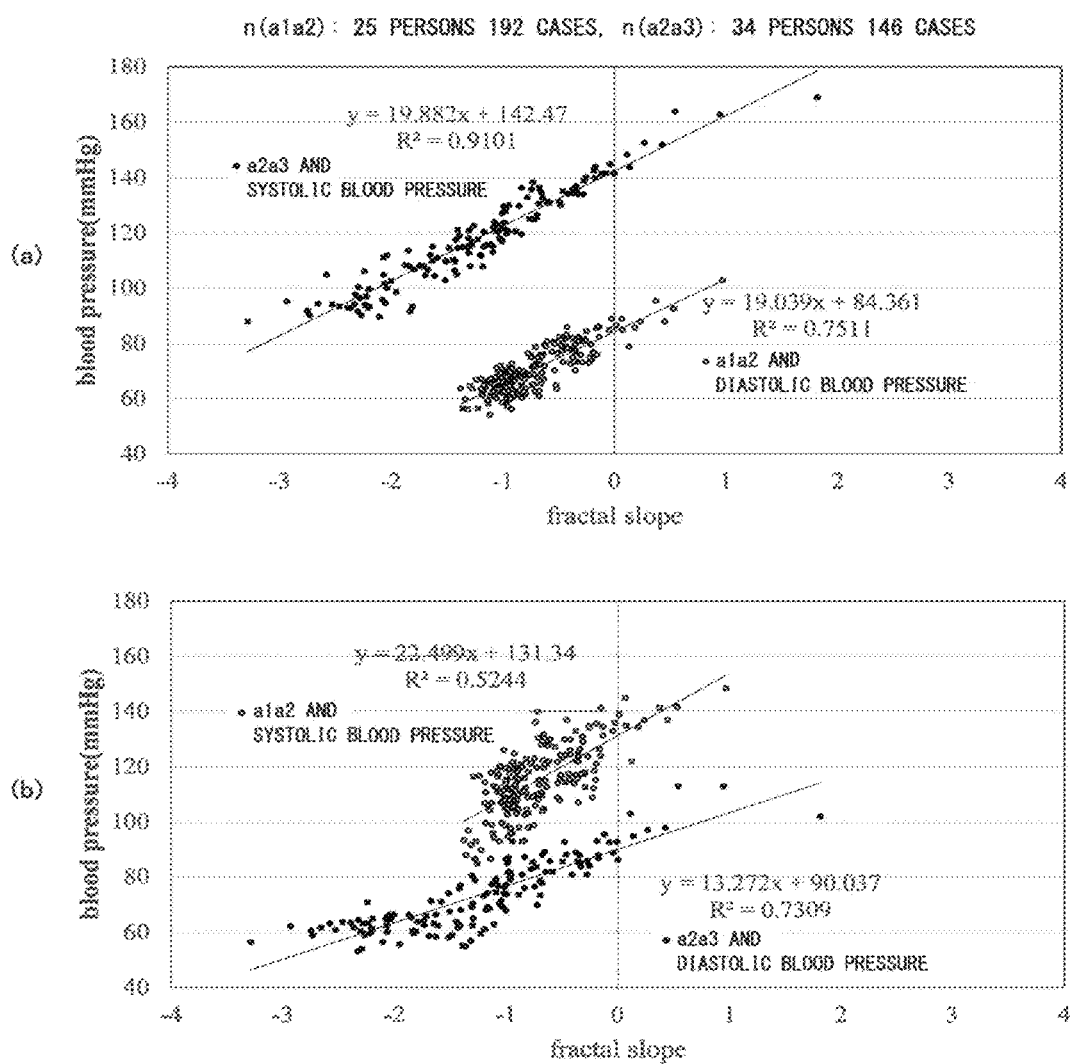
FIG. 18(a) is a chart illustrating the correlation data for blood pressure estimation in FIG. 16 again.
FIG. 18(b) is comparison data in whose generation, the correspondence relation of the systolic blood pressure and the diastolic blood pressure of a brachial blood pressure monitor versus the fractal slopes (FS) is reversed from that in FIG. 18(a).

Here, in FIG. 18(a), the correlation data for blood pressure estimation in FIG. 16 is illustrated again for comparison with FIG. 18(b). FIG. 18(b) illustrates plot groups which are obtained when the systolic blood pressures measured with the brachial blood pressure monitor are plotted versus the values of the a1a2-based fractal slope (FS) and the diastolic blood pressures measured with the brachial blood pressure monitor are plotted versus the values of the a2a3-based fractal slope (FS), in an opposite manner to FIG. 18(a). In FIG. 18(b), the regression line of the plot group resulting from the plotting of the systolic blood pressures versus the values of the a1a2-based fractal slope (FS) was y=22.499x+131.34 and its coefficient of determination was 0.5244, indicating a greatly inferior correlation as compared with FIG. 18(a). Further, the regression line of the plot group resulting from the plotting of the diastolic blood pressures versus the values of the a2a3-based fractal slopes (FS) was y=13.272x+90.037 and its coefficient of determination was 0.7309. The value of the coefficient of determination was slightly lower, and a y intercept was slightly higher than 90. Further, it is seen that, in FIG. 18(a), the slopes of the regression lines of the systolic blood pressure and the diastolic blood pressure are substantially the same, while, in the method in FIG. 18(b), the slopes of the regression lines of the systolic blood pressure and the diastolic blood pressure are greatly different. In other words, in the case of the method in FIG. 18(b), a data structure having almost no difference between the systolic blood pressure and the diastolic blood pressure exists and it is seen that reliability as the correlation data for estimating them in a clearly distinguished manner is inferior. Therefore, it is appropriate to use the value of the a1a2-based fractal slope (FS) for the diastolic blood pressure estimation and use the value of the a2a3-based fractal slope (FS) for the systolic blood pressure estimation as in this embodiment.

Figure 19:
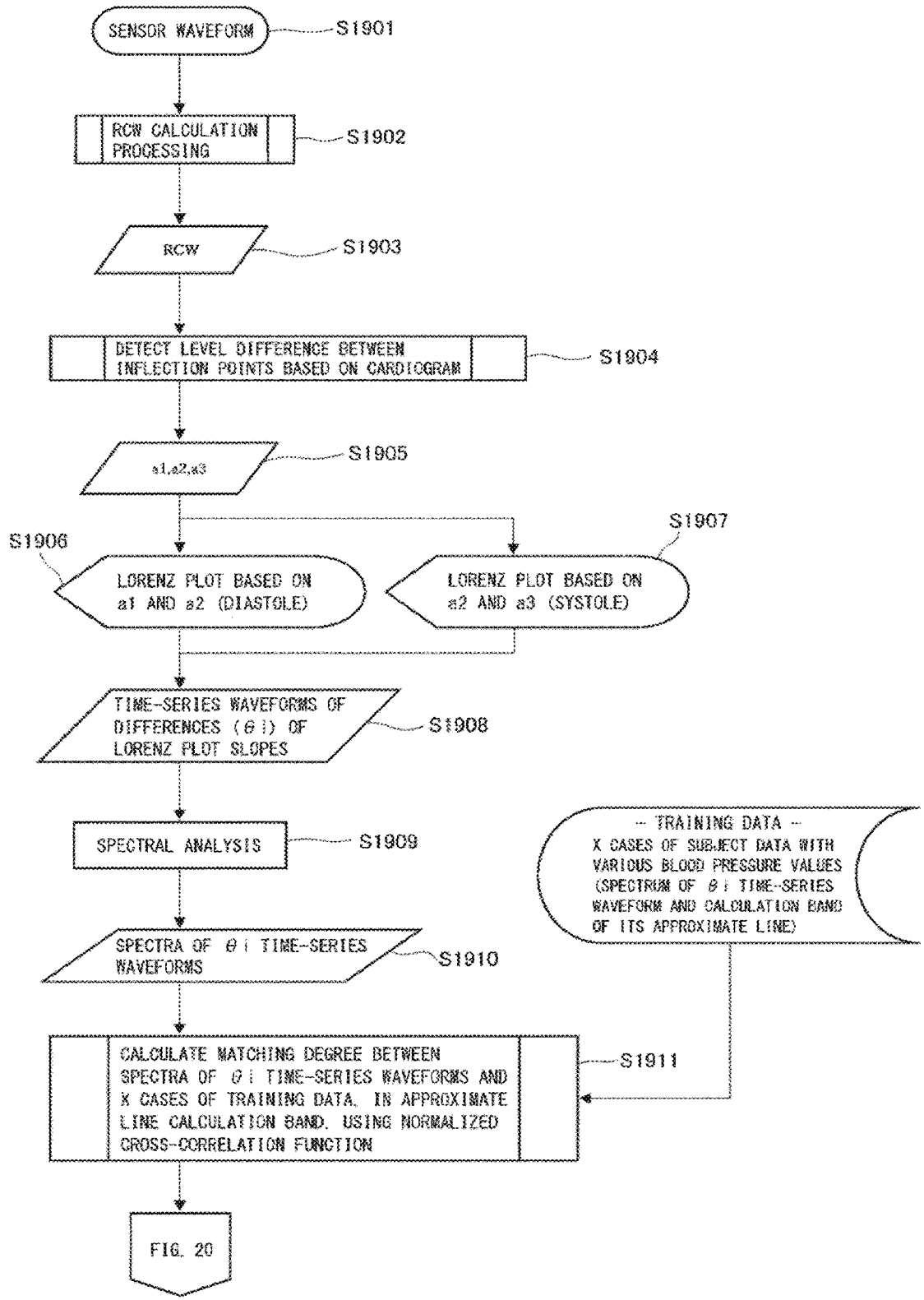
FIG. 19 is an explanatory flowchart of a blood pressure estimation process.
Figure 20:
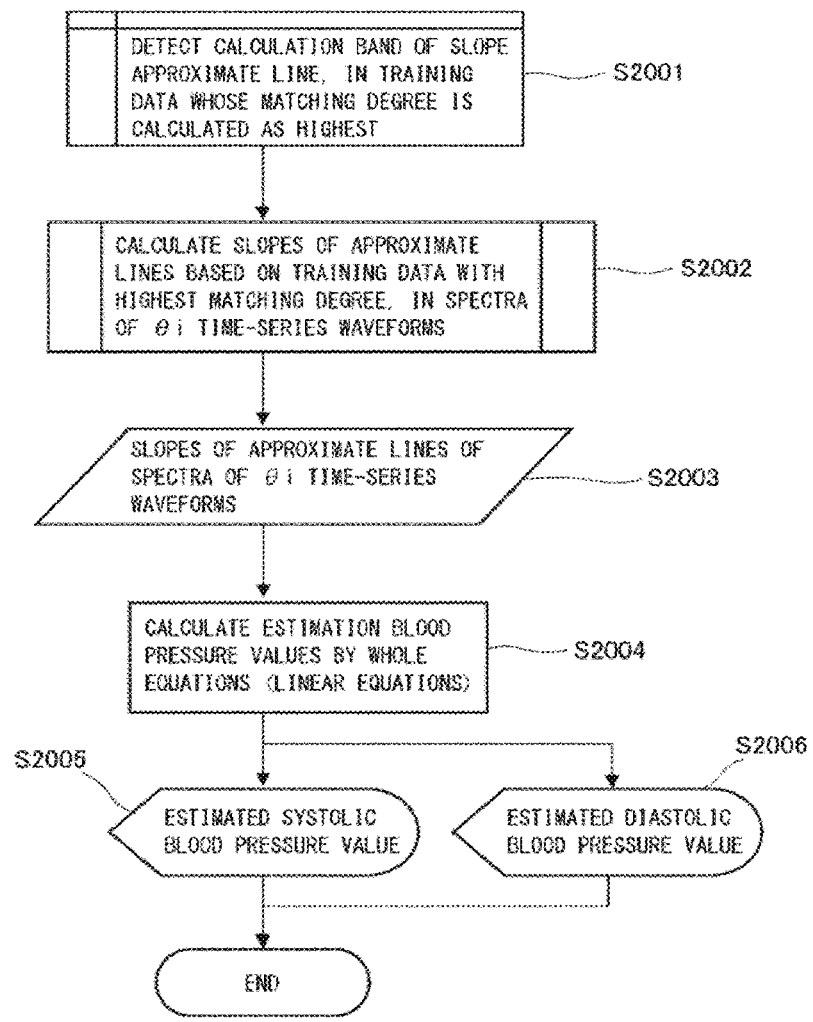
[FIG. 20] is an explanatory flowchart of the blood pressure estimation process continuing from FIG. 19.

Next, based on the flowcharts in FIG. 19 and FIG. 20, a blood pressure estimation process will be specifically described. First, a person whose blood pressure is to be estimated (blood pressure estimation subject) is seated on a chair or the like for measurement on which the biological signal detection unit 10 of the biological signal measurement device 1 for detecting a dorsal body surface pulse wave is provided on its back part as described above. Further, the electrodes of the cardiograph 300 are put on the chest of the blood pressure estimation subject, and the setting is made such that his/her cardiogram waveform data is transmitted to the blood pressure estimation device 100.

When the measurement starts, the blood pressure estimation device 100 receives a dorsal body surface pulse wave (sensor waveform) of the blood pressure estimation subject from the biological signal measurement device 1 (S1901). Then, the filtering means 210 in the blood pressure estimation device 100 filters the received sensor waveform (S1902) into RCW (S1903). Next, as illustrated in FIG. 4, the scatter plot generation means 221 of the blood flow rate change index calculation means 220 specifies the timing of the R wave in the cardiogram waveform data obtained from the cardiograph 300 (S1904) and based on this, finds the aforesaid total amplitudes a1, a2, a3 (S1905). Next, the scatter plot generation means 221 generates a scatter plot (Lorenz plot) using a1 and a2 and a scatter plot (Lorenz plot) using a2 and a3 (S1906, S1907). Next, the scatter plot slope calculation means 222 finds slopes θ1 of regression lines of the scatter plots, and the fluctuation analysis means 231 of the fluctuation index calculation means 230 generates time-series waveforms of θ1 for diastole and systole (S1908). Next, the fluctuation analysis means 231 performs frequency analysis (spectral analysis) (S1909) to generate fluctuation analysis plots which are the spectra of the θ1 time-series waveforms, for diastole and systole (S1910).

Figure 21:
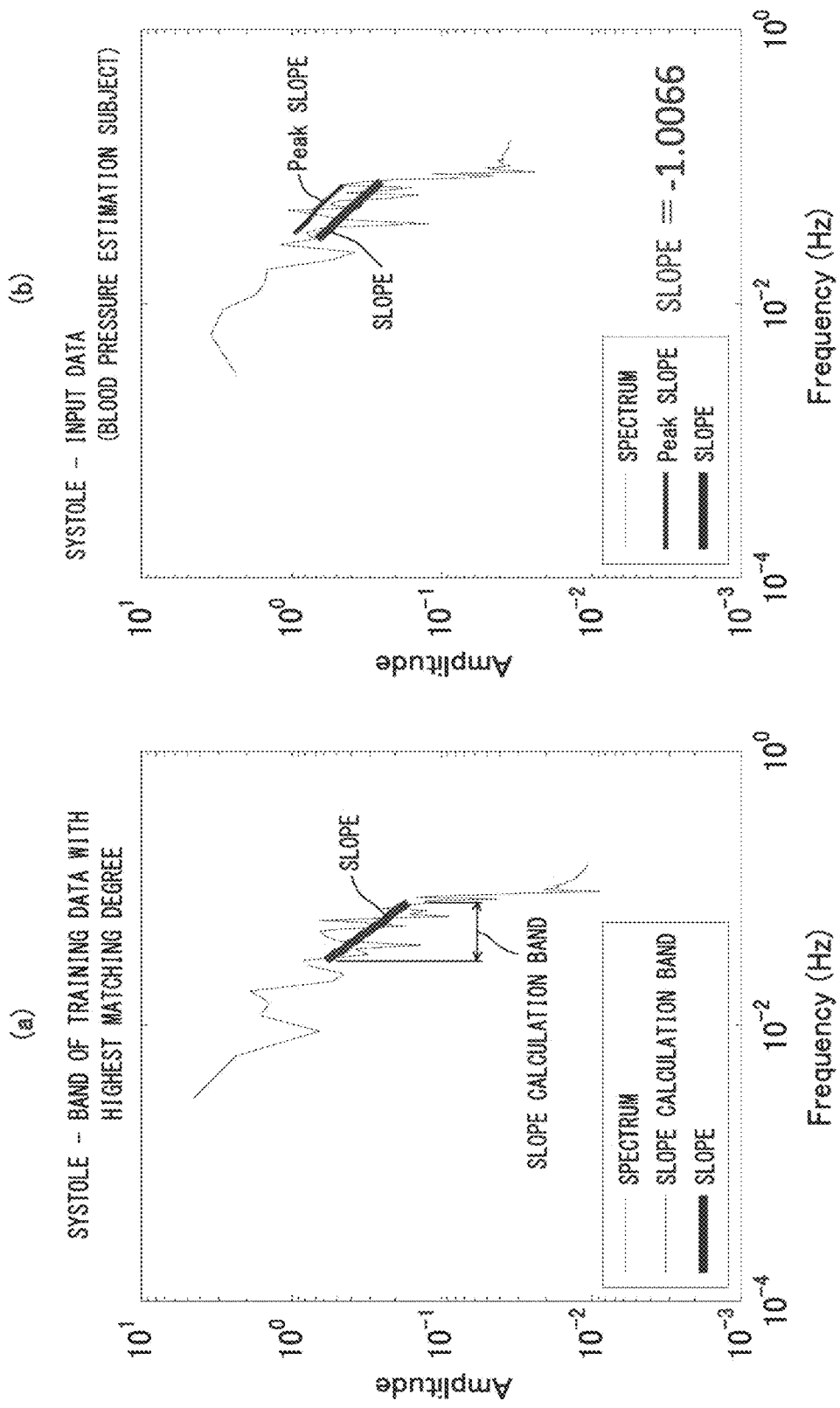
FIGS. 21(a), (b) are explanatory charts of a method of finding the fractal slope.

Next, the fluctuation analysis plot slope calculation means 232 accesses the database in the storage unit (see FIG. 2) to collate the fluctuation analysis plots (spectra) for diastole and systole of the blood pressure estimation subject which are found at S1910, with the training data of the fluctuation analysis plots (spectra) (S1911). As described above, to help to find an appropriate slope (fractal slope) of the regression line B for each subject, in each of the training data, a predetermined frequency band suited to his/her property is set in the range belonging to VLF to LF. Therefore, at S1911, the fluctuation analysis plots (for diastole and for systole) of the blood pressure estimation subject which are found at S1910 are collated in the frequency band range set in the training data, and training data with a high matching degree is extracted using a normalized cross-correlation function. Next, the fluctuation analysis plot slope calculation means 232 applies the frequency band set in the extracted training data to the fluctuation analysis plots (for diastole and for systole) of the blood pressure estimation subject which are found at S1910 (S2001), to find the slopes of the regression lines B in this range as the fractal slopes (FS) (S2002, S2003). FIGS. 21 illustrate examples thereof, and FIG. 21(b) illustrates the fluctuation analysis plot (spectrum) of the blood pressure estimation subject. FIG. 21(a) illustrates an example of the training data, the thick line represents the regression line B of this training data, and the matching degrees of the fluctuation analysis plots (spectra) are compared in the same frequency band as the frequency band in which the regression line B of the training data is drawn. Since the frequency band set in the training data differs depending on each training data as described above, the matching degrees of all the training data are compared, and the same frequency band as the frequency band set in the training data with the highest matching degree is set in the fluctuation analysis plot of the blood pressure estimation subject in FIG. 21(b), the regression line B is drawn in this frequency band, and its slope is found as the fractal slope.

Note that the aforesaid matching degree comparison method with the training data is only an example, and in the comparison of the matching degrees, it is also possible to determine the matching degree for the entire fluctuation analysis plot (spectrum) belonging to VLF to LF and use a frequency band set in the training data that is determined as having the high matching degree, in the fluctuation analysis plot of the blood pressure estimation subject.

Next, the estimation means 240 operates to access the correlation data for blood pressure estimation, which is illustrated in FIG. 16 or FIG. 17, stored in the storage unit (S2004) and substitutes the fractal slopes (FS) in the correlation equations for diastolic and systolic blood pressure estimation. Consequently, it is possible to find the diastolic blood pressure and the systolic blood pressure of the blood pressure estimation subject (S2005, S2006).

Figure 22:
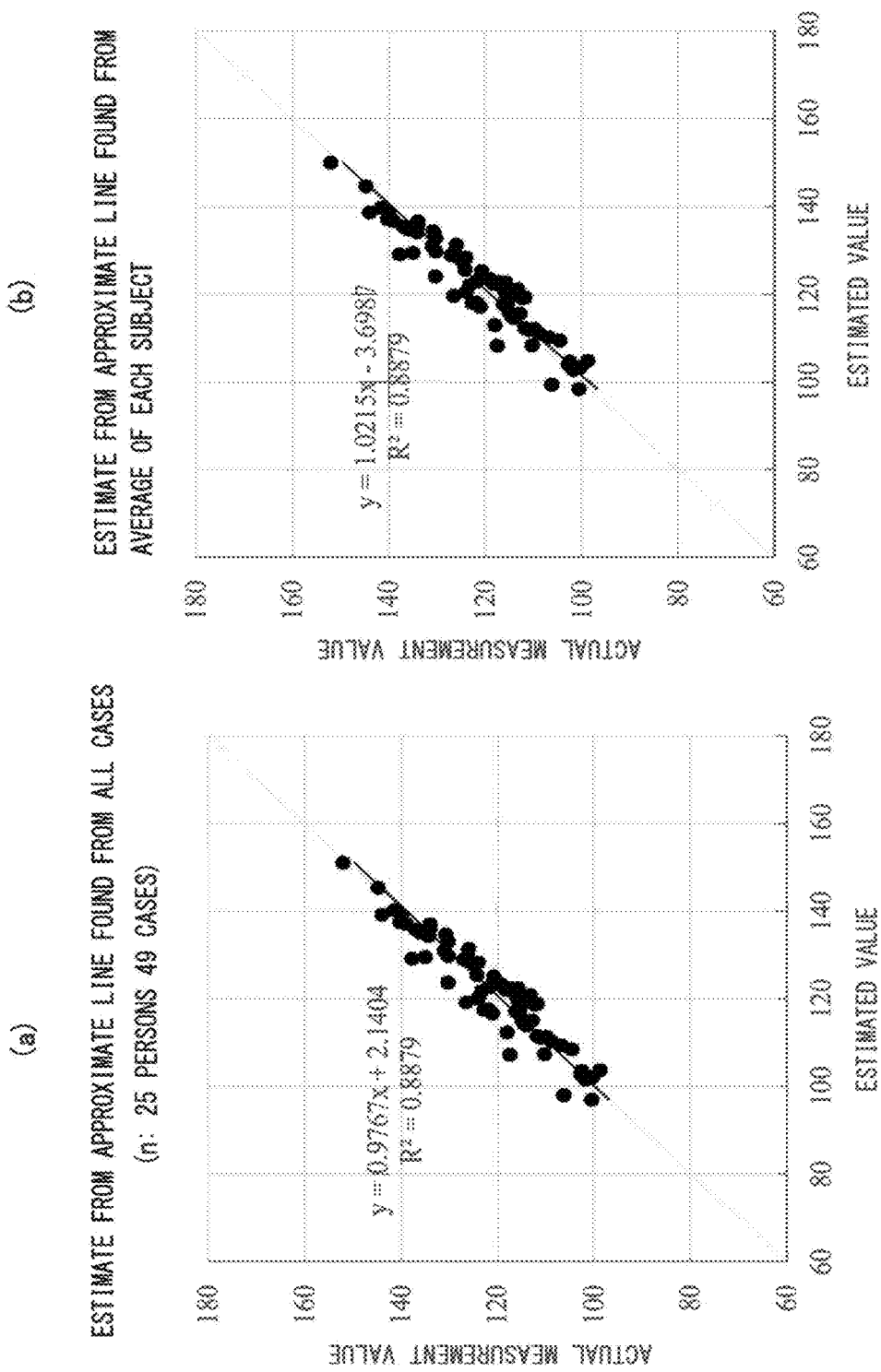
FIGS. 22(a), (b) are graphs in which estimation values of blood pressure estimated by the aforesaid embodiment and actual measurement values of brachial blood pressure are compared.

FIG. 22(a) is a chart in which the systolic blood pressures which are estimated regarding a plurality of blood pressure estimation subjects (25 persons, 49 data) according to the steps illustrated in FIG. 19 to FIG. 20 are compared with actual measurement values of their brachial blood pressures. In FIG. 22(a), the blood pressures are estimated using the correlation data for blood pressure estimation in FIG. 16 found using all the cases, and in FIG. 22(b), the blood pressures are estimated using the correlation data for blood pressure estimation in FIG. 17 found using the average values. In both of them, the slope is close to 1 and the coefficient of determination is also high, which shows that the blood pressure estimated by the method of this embodiment has a very high correlation with the brachial blood pressure.

Figure 23:
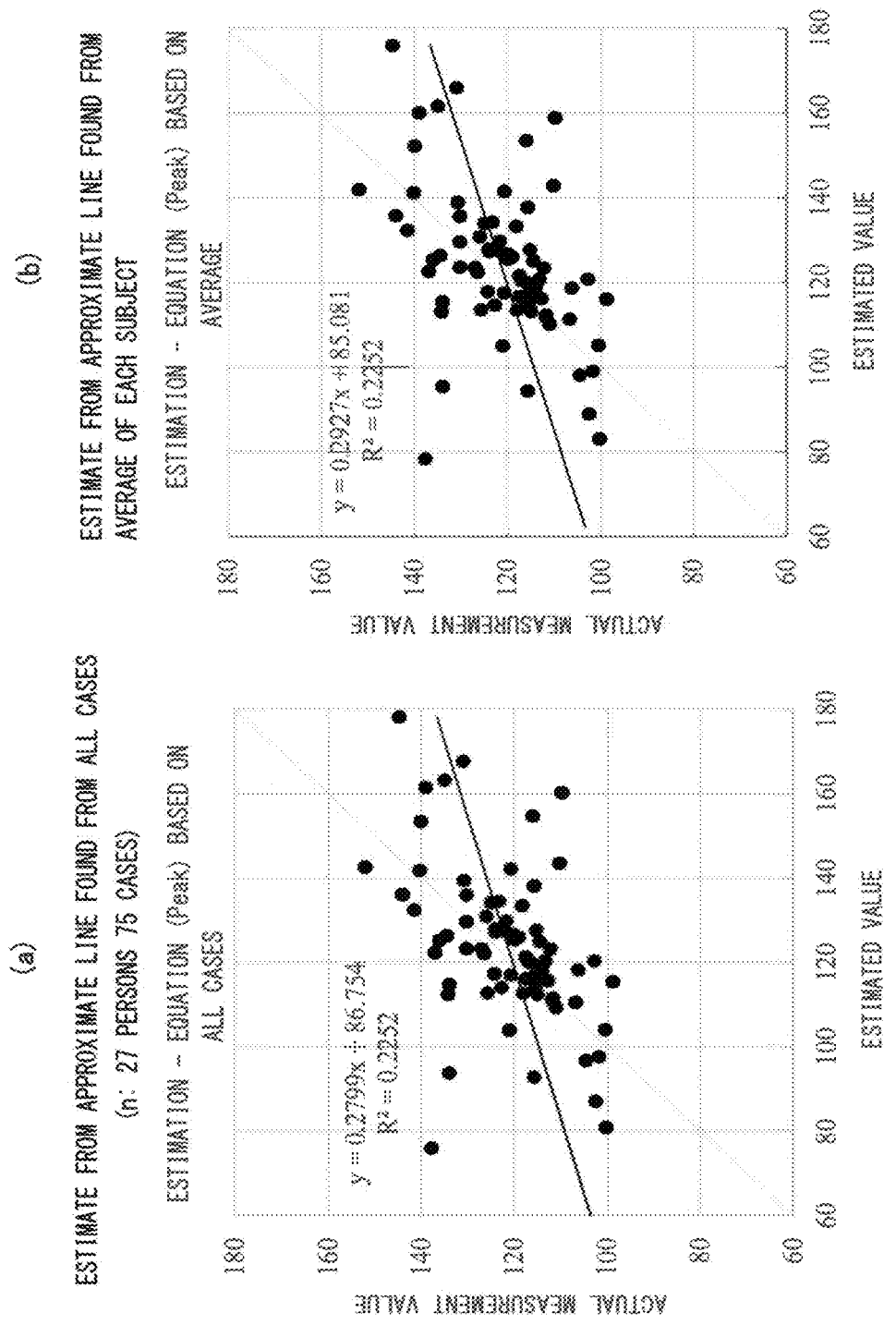
FIGS. 23(a), (b) are graphs in which estimation values of blood pressure are compared with actual measurement values of brachial blood pressure, the estimation values being found with a slope of a regression line whose fractal slope is to be found being made different from that in FIGS. 22.
Figure 24:
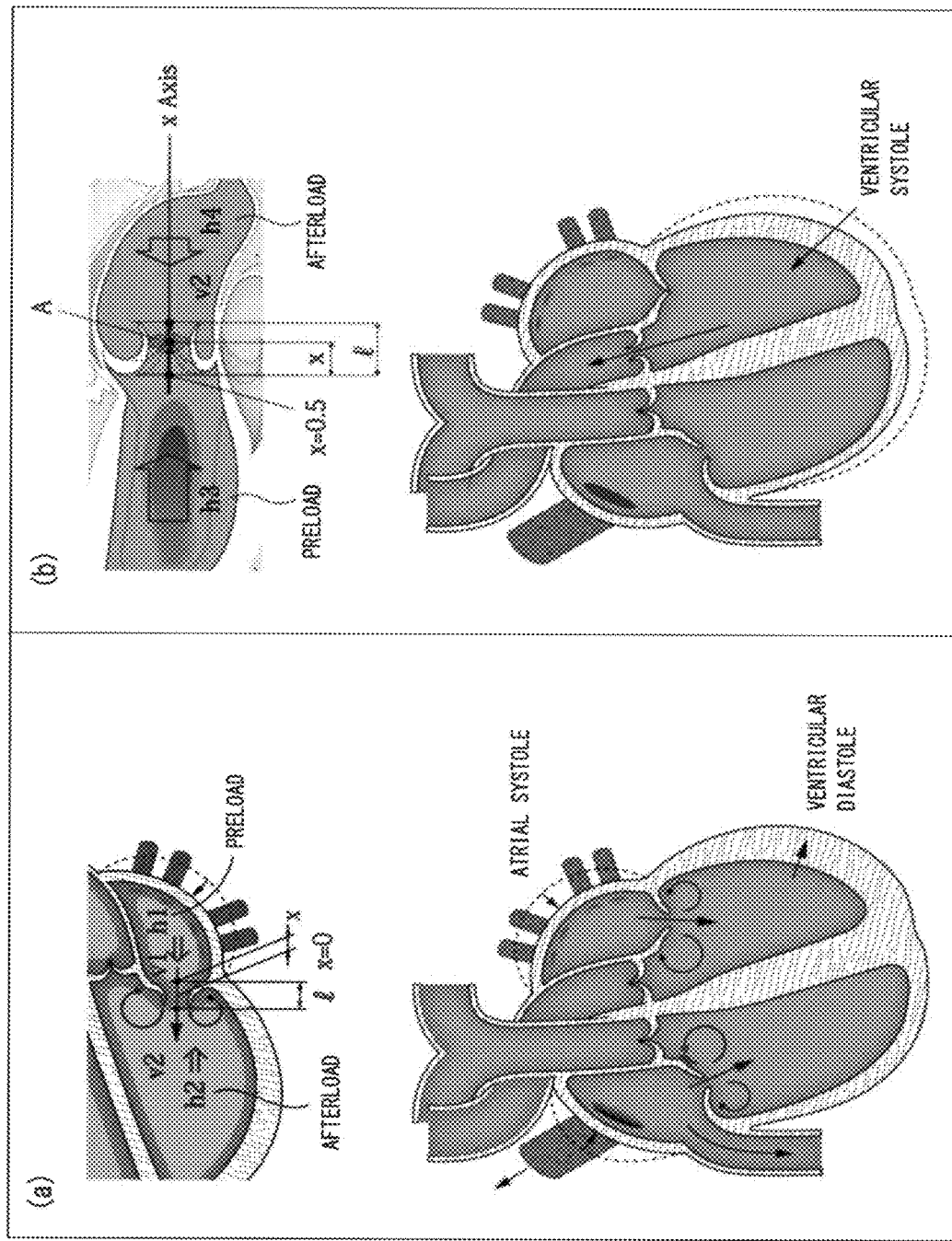
FIGS. 24(a), (b) are views illustrating volume changes of the atria and the ventricles and the movement of blood during a period from the ventricular filling period up to the release of a valve at the isovolumetric systole.

On the other hand, FIGS. 23(a), (b) are charts in which estimated systolic blood pressures and actual measurement values of the brachial blood pressures of blood pressure estimation subjects (27 persons, 75 data) are compared, the systolic blood pressures being estimated in such a manner that, at the time of the calculation of the slope in the predetermined frequency band which is set with reference to the training data (S2001, S2002 in FIG. 20), instead of finding the slope of the regression line regarding the entire waveform components in the fluctuation analysis plot in this frequency band (indicated simply as "slope" in the drawing), a slope of a regression line regarding only the upper peak points in the drawing in these waveform components (indicated as "peak slope" in the drawing) is found as illustrated in FIG. 21(b). Note that, in FIG. 23(a), the correlation data for blood pressure estimation in FIG. 16 using all the cases is used, and in FIG. 23(b), the correlation data for blood pressure estimation in FIG. 17 using the average values is used. As is apparent from FIGS. 23(a), (b), the correlation between the estimated values and the actual measurement values in this case was very low. Therefore, regarding the waveform components in the predetermined frequency band in the fluctuation analysis plot, the slope of the regression line B regarding the entire waveform components is preferably adopted as the fractal slope (FS) as described above.

According to this embodiment, the correlation data for blood pressure estimation (for diastolic blood pressure estimation, for systolic blood pressure estimation) showing the relations between the brachial blood pressures and the fractal slopes (FS) of a plurality of subjects are generated and are stored as described above and then, only by finding the fractal slope (FS) of a blood pressure estimation subject, it is possible to estimate his/her blood pressure in a non-constraining manner and in real time by collating the fractal slope with the correlation data and also to estimate the blood pressure continuously.

Therefore, by providing the biological signal detection unit 10 of the biological signal measurement device 1 on, for example, a bed, a back part of a chair, or other human body supporting means, it is possible to estimate the blood pressure of a subject any time. Therefore, it is also possible to detect a sudden change in the blood pressure of the subject and also know a change in the blood pressure while he/she is sleeping. Needless to say, it is possible to notify information on the estimated blood pressure to any display device such as a monitor or a warning light or to a terminal device of a manager or the like through a communication means (not illustrated) built in or connected to the blood pressure estimation device 100.

EXPLANATION OF REFERENCE SIGNS

1 biological signal measurement device
10 biological signal detection unit
1 core pad
12 spacer pad
14 sensor
100 blood pressure estimation device
200 biological signal processing means
210 filtering means
220 blood flow rate change index calculation means
221 scatter plot generation means
222 scatter plot slope calculation means
230 fluctuation index calculation means
231 fluctuation analysis means
232 fluctuation analysis plot slope calculation means
240 estimation means

The invention claimed is:

1. A blood pressure estimation method comprising:
receiving a biological signal from a biological signal measurement device configured to contact with a dorsal part of a person to capture the biological signal propagated through a body surface of the dorsal part in a non-constraining manner;
filtering, with a predetermined frequency band, a biological signal time-series waveform of the biological signal into a filter-processed waveform in which a cardiac cycle is manifested;
collating the filter-processed waveform with cardiogram waveform data measured simultaneously with the received biological signal and obtained from a cardiograph, specifying a waveform component in a range of the biological signal time-series waveform from a ventricular filling period to isovolumetric systole in the filter-processed waveform, and finding an index regarding vibration ascribable to a blood flow rate change in a period from the ventricular filling period to the isovolumetric systole;
finding an index time-series waveform of the index regarding the vibration ascribable to the blood flow rate change and thereafter finding an index regarding fluctuation indicating a change in the found time-series waveform; and
estimating a blood pressure of the person based on the index regarding the fluctuation by using correlation data for the blood pressure estimation which is stored in a storage unit in advance and shows a relation between the index regarding the fluctuation and the blood pressure estimation.

2. The blood pressure estimation method according to claim 1, wherein the biological signals are received continuously from the biological signal measurement device, and the blood pressure of the person is continuously estimated.

3. The blood pressure estimation method according to claim 1, wherein the biological signal is captured while a biological signal detection unit of the biological signal measurement device is disposed in a range from a place corresponding to a position of a clavicle to a place corresponding to a position of a xiphisternum, on the dorsal part of the person.

4. A non-transitory computer readable medium storing a program causing a computer to function as a blood pressure estimation device by causing the computer to execute a biological signal processing procedure for receiving a biological signal from a biological signal measurement device configured to contact with a dorsal part of a person to capture the biological signal propagated through a body surface of the dorsal part in a non-constraining manner, and analyzing the received biological signal,
wherein, as the biological signal processing procedure, the computer is caused to execute:
a procedure for filtering, with a predetermined frequency band, a biological signal time-series waveform of the biological signal into a filter-processed waveform in which a cardiac cycle is manifested;
a procedure for collating the filter-processed waveform with cardiogram waveform data measured simultaneously with the received biological signal and obtained from a cardiograph, specifying a waveform component in a range of the biological signal time-series waveform from a ventricular filling period to isovolumetric systole in the filter-processed waveform, and finding an index regarding vibration ascribable to a blood flow rate change in a period from the ventricular filling period to the isovolumetric systole;

a procedure for finding an index time-series waveform of the index regarding the vibration ascribable to the blood flow rate change and finding an index regarding fluctuation indicating a change in the found time-series waveform; and a procedure for estimating a blood pressure of the person based on the index regarding the fluctuation by using correlation data for the blood pressure estimation which is stored in a storage unit in advance and shows a relation between the index regarding the fluctuation and the blood pressure estimation.

5. The computer readable medium according to claim 4, wherein, in the biological signal processing procedure, the computer is caused to execute the estimation of the blood pressure of the person continuously by using the biological signals continuously received.

6. The computer readable medium according to claim 4, wherein, in the procedure for finding the index regarding the fluctuation, the computer is caused to execute:

a procedure for finding the index time-series waveform of the index regarding the vibration ascribable to the blood flow rate change, frequency-analyzing the index time-series waveform, and generating a fluctuation analysis plot which is a result of the frequency analysis, on a power spectrum-frequency log-log graph; and a procedure for finding a slope of a regression line of the fluctuation analysis plot, the slope of the regression line of the fluctuation analysis plot being the index regarding the fluctuation.

7. The computer readable medium according to claim 6, wherein, as the slope of the regression line of the fluctuation analysis plot, a slope of the regression line in predetermined frequency band belonging to a range from very-low-frequency band (VLF) to low-frequency band (LF) is found, the found slope being the index regarding the fluctuation.

8. The computer readable medium according to claim 4, wherein, in the procedure for finding the index regarding the vibration ascribable to the blood flow rate change, the computer is caused to execute:

a procedure for specifying one set or more of two of the waveform components in the range of the biological signal time-series waveform corresponding to the ventricular filling period to the isovolumetric systole, in the biological signal, and generating a scatter plot by using total amplitudes of the two waveform components; and a procedure for finding a slope of a regression line of a plot group plotted in the scatter plot, the slope of the regression line of the plot group being the index regarding the vibration ascribable to the blood flow rate change.

9. The computer readable medium according to claim 8, wherein, as the procedure for generating the scatter plot, a procedure is executed for generating a first scatter plot using total amplitudes of the two waveform components at the time of atrial contraction in the ventricular filling period and a second scatter plot using total amplitudes of the two waveform components corresponding to a timing that is after the two waveform components used in the first scatter plot and near an atrioventricular valve closure time which is a shift time to the isovolumetric systole, and wherein, in the procedure for finding the index regarding the fluctuation, diastolic blood pressure is estimated from a fluctuation index found using the first scatter plot, and systolic blood pressure is estimated from a fluctuation index found using the second scatter plot.

\* \* \* \* \*